US010561492B2

(12) United States Patent
Galstian et al.

(10) Patent No.: US 10,561,492 B2
(45) Date of Patent: Feb. 18, 2020

(54) REPROGRAMMABLE TUNEABLE LIQUID CRYSTAL LENS INTRAOCULAR IMPLANT AND METHODS THEREFOR

(71) Applicant: LENSVECTOR INC., Sunnyvale, CA (US)

(72) Inventors: Tigran Galstian, Quebec (CA); Howard Earhart, Saratoga, CA (US)

(73) Assignee: LENSVECTOR INC., Sunnyvale, CA (US)

( * ) Notice: Subject to any disclaimer, the term of this patent is extended or adjusted under 35 U.S.C. 154(b) by 360 days.

(21) Appl. No.: 14/924,950

(22) Filed: Oct. 28, 2015

(65) Prior Publication Data

US 2016/0106533 A1    Apr. 21, 2016

Related U.S. Application Data

(63) Continuation of application No. PCT/CA2014/050409, filed on Apr. 30, 2014.

(60) Provisional application No. 61/817,660, filed on Apr. 30, 2013.

(51) Int. Cl.
*A61F 2/16* (2006.01)

(52) U.S. Cl.
CPC .......... *A61F 2/1624* (2013.01); *A61F 2/1635* (2013.01)

(58) Field of Classification Search
None
See application file for complete search history.

(56) References Cited

U.S. PATENT DOCUMENTS

| 8,216,309 | B2 | 7/2012 | Azar | |
|---|---|---|---|---|
| 2006/0095128 | A1* | 5/2006 | Blum | A61F 2/1627 623/6.37 |
| 2008/0180630 | A1* | 7/2008 | Clarke | G02C 7/083 349/201 |
| 2009/0204207 | A1* | 8/2009 | Blum | G02C 7/08 623/4.1 |
| 2012/0140037 | A1 | 6/2012 | Galstian et al. | |
| 2012/0206691 | A1* | 8/2012 | Iwai | G02C 7/041 351/159.03 |

(Continued)

FOREIGN PATENT DOCUMENTS

WO    WO 2012/122411 A1    9/2012

OTHER PUBLICATIONS

Carlo et al., Age-Related Changes of the Human Eye, 2008, Springer, abstract.

(Continued)

*Primary Examiner* — Leslie Lopez
(74) *Attorney, Agent, or Firm* — J-Tek Law PLLC; Jeffrey D. Tekanic; Scott T. Wakeman

(57) ABSTRACT

A reprogrammable intraocular adaptive lens prosthesis apparatus is provided. The apparatus includes a tunable liquid crystal lens (TLCL) encapsulated in the intraocular prosthesis with control electronics and a power source or in the intraocular prosthesis with a control signal receiver while an external control electronics package transmits the control signal. The TLCL is driven in response to a stimulus signal to provide accommodation. The TLCL corrects other visual shortcomings of the natural eye. The intraocular prosthesis has a remote programmable TLCL controller configured to recalibrate the TLCL to compensate for dynamic adaptation of the eye over time.

23 Claims, 25 Drawing Sheets

(56) References Cited

U.S. PATENT DOCUMENTS

2014/0327875 A1   11/2014   Blum et al.

OTHER PUBLICATIONS

Faith A. Hayden, Electronic IOLs: The future cataract surgery, IOLs Feb. 2012, 58-60.
Hengerer FH et al., Evaluation of the Calhoun Vision UV Light Adjustable Lens implanted following cataract removal, J Refract Surg. Oct. 2010;26(10):716-21. doi: 10.3928/1081597X-20100408-02. Epub Apr. 15, 2010. abstract.
PCT/CA2014/050409 International preliminary report dated Jul. 9, 2015.
PCT/CA2014/050409 International search report with related claims dated Aug. 19, 2014.
PCT/CA2014/050409 written opinion dated Aug. 19, 2014.
Samuel Masket, Accommodating IOLs: Emerging Concepts and Designs, Cataract & Refractive Surgery Today | Jul. 2004, 32-37.

\* cited by examiner

Mold Array

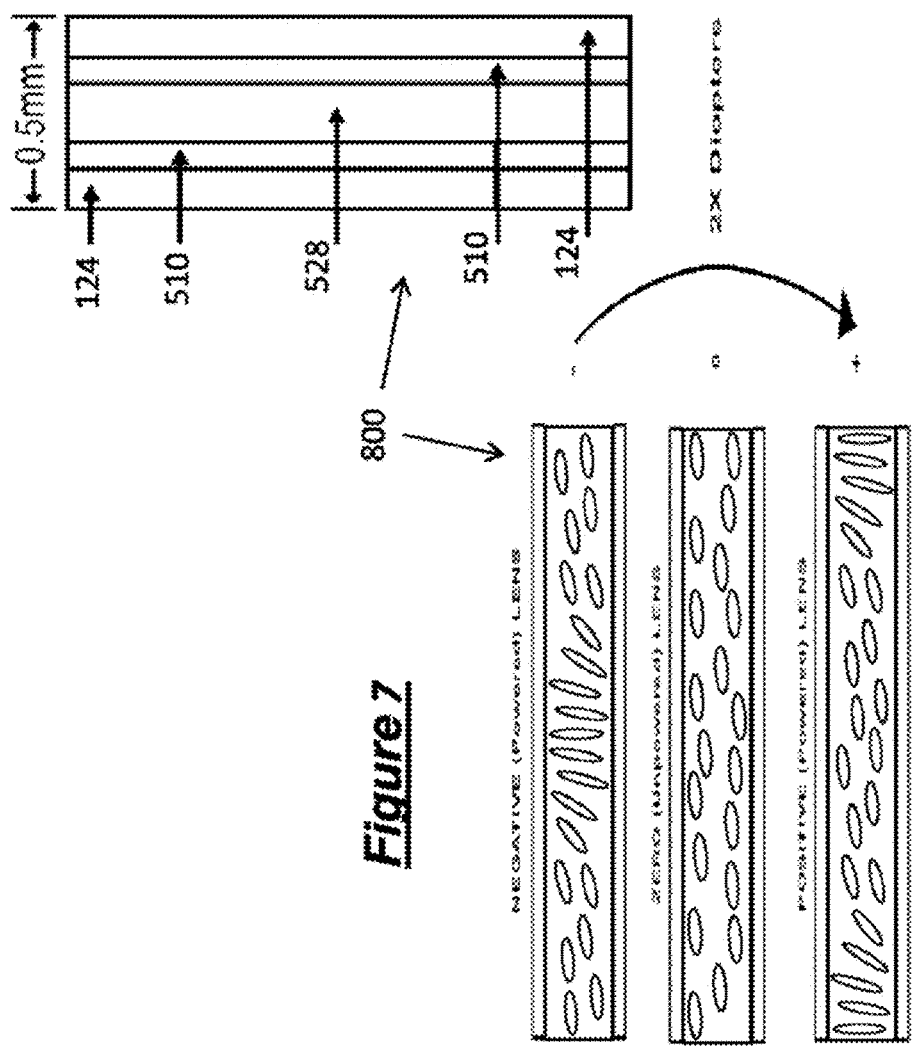

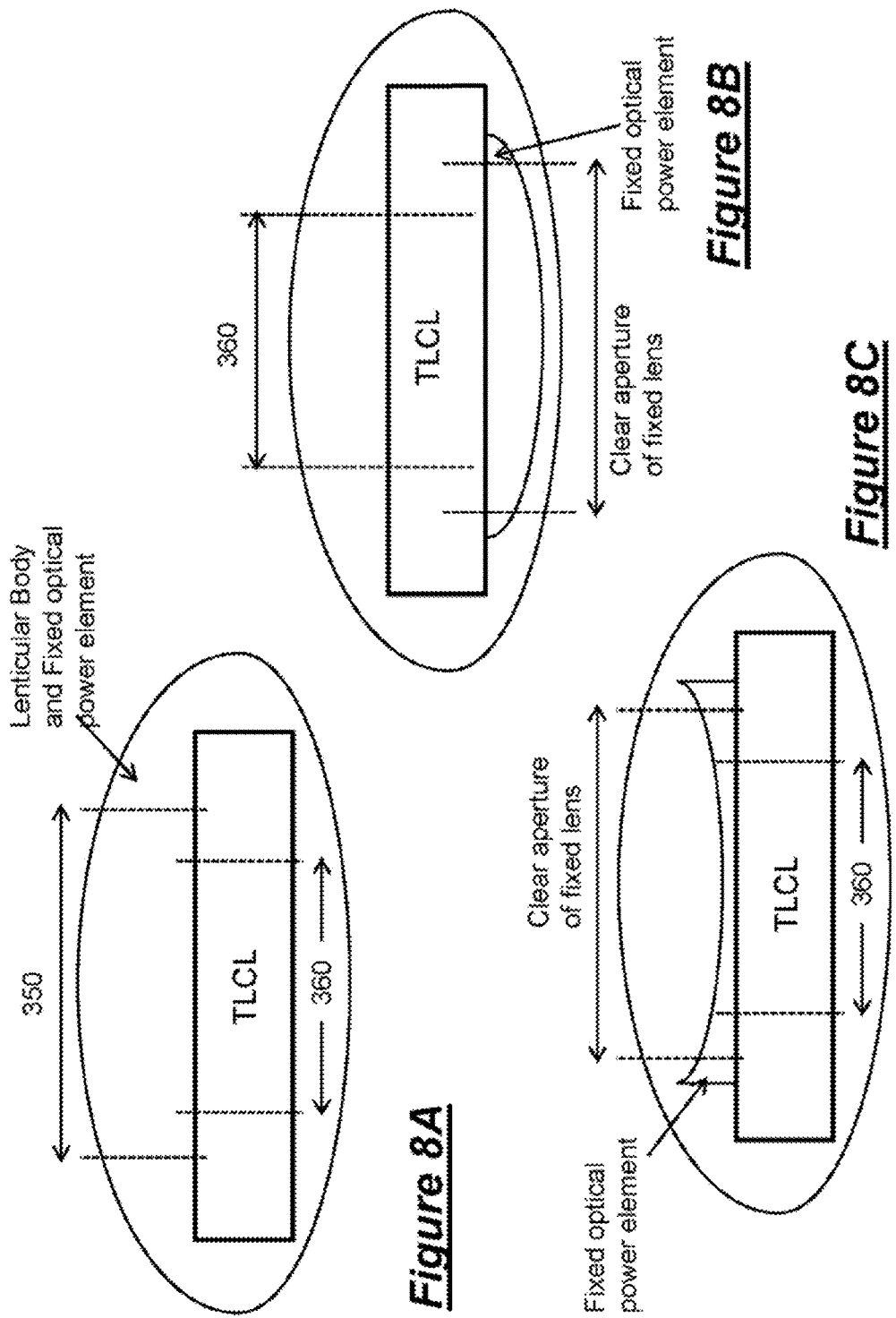

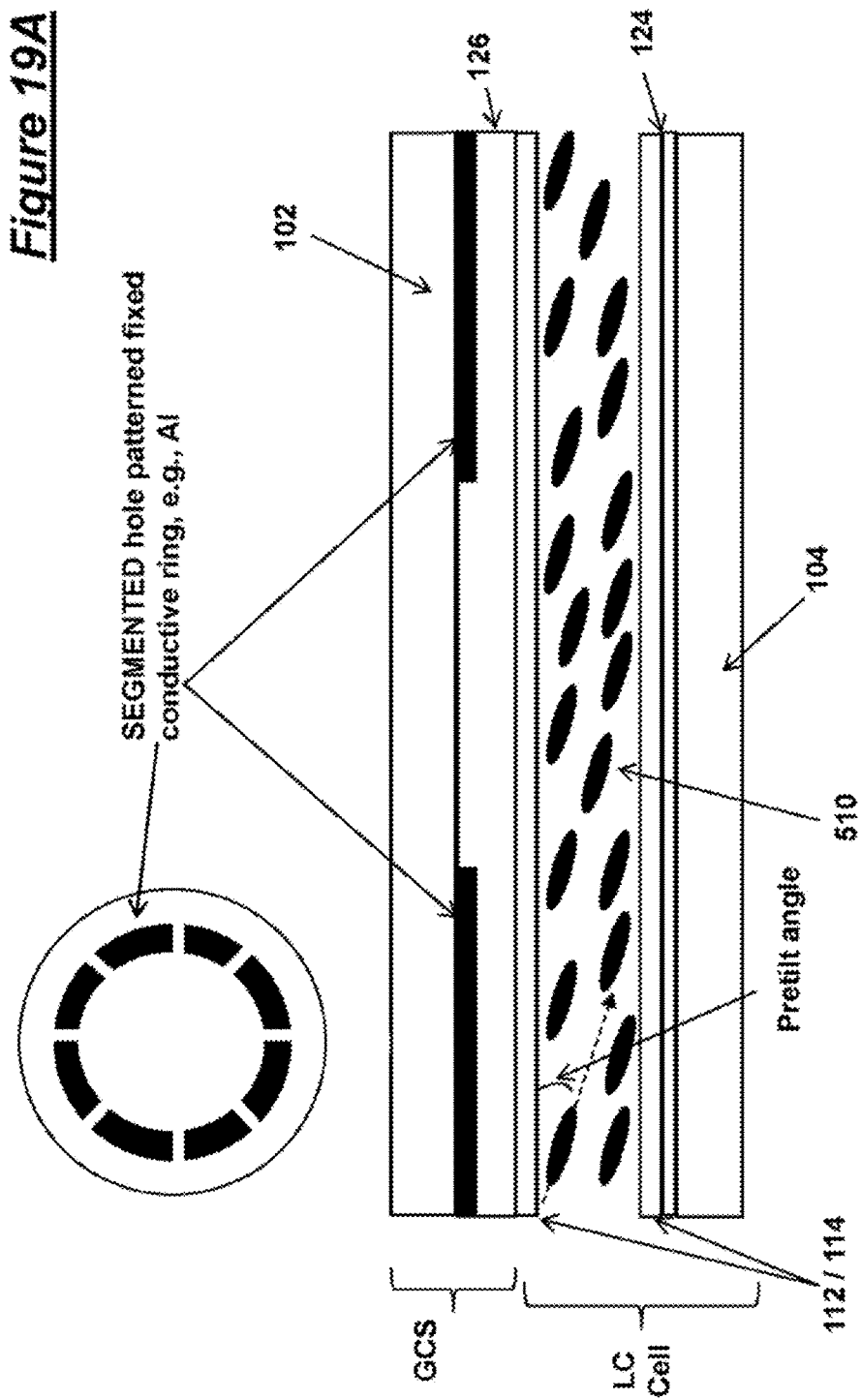

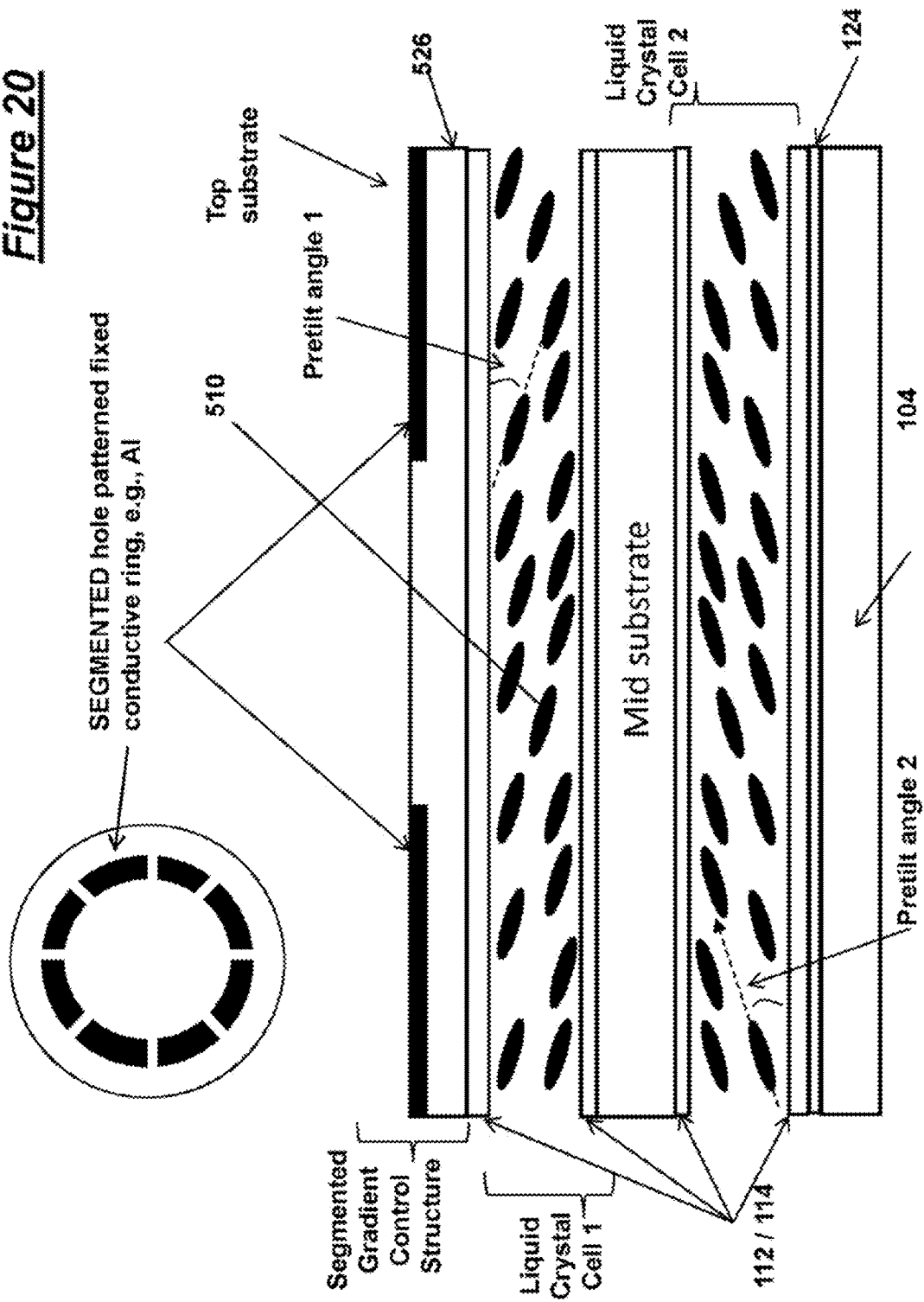

REPROGRAMMABLE TUNEABLE LIQUID CRYSTAL LENS INTRAOCULAR IMPLANT AND METHODS THEREFOR

This application claims priority to U.S. provisional patent application 61/817,660, filed Apr. 30, 2013.

TECHNICAL FIELD

This invention relates to vision correction, and in particular to reprogrammable active intraocular implant assisted vision apparatus and methods therefor.

BACKGROUND

The human eye is known to naturally evolve with time. This includes aging effects, eye surgery or can result from accidents or from exposure to atypical or harmful environmental conditions. This evolution may change the geometry of the eye optics, the dynamics of its operation and its accommodative capacity. Age-related eye changes are described for example in "Age-Related Changes of the Human Eye" by Carlo A. P. Cavallotti, Luciano Cerulli, 2008, Springer. Changes in the geometry of the eye optics (e.g., thickness of the crystalline lens, its position, etc.) may be also provoked by various interventions, such as intra ocular surgery or a Lasik operation. Obviously, those interventions have the goal to improve the vision. However the uncontrolled (post-surgery or age related) changes are generally degrading the vision.

One of the possible ways of addressing this problem is the repeated surgical intervention, which may create further complication or simply be impossible. Another way of proceeding is to test the vision at different time scales and to order corresponding glasses or contact lenses if it is in principle possible to correct the resulting refractive errors.

An interesting alternative way was proposed that is based on the light adjustable lens (LAL), see, for example, J Refract Surg. 2010 October; 26(10):716-21. doi: 10.3928/1081597X-20100408-02. Epub 2010 Apr. 15. Evaluation of the Calhoun Vision UV Light Adjustable Lens implanted following cataract removal. Hengerer F H, Conrad-Hengerer I, Buchner S E, Dick H B. This may be an intra-ocular lens (IOL) that is composed of UV sensitive material. In this case, the lens is inserted in the eye (during the cataract surgery) and the patients are asked to wear UV protective glasses. After few weeks, the refractive analysis of patients has identified the refractive errors to be corrected. This was done by the exposition of IOL (the LAL) by UV light. The material of the LAL is photopolymerized causing the shape and hence the power of the lens to change. In principle this operation may be repeated one or two times. However, the LAL is finally "locked" and no more modifications are possible.

While this is a very interesting approach. It still remains rather difficult (and not user friendly) and also its reprogramming capacity is very limited in time.

Various accommodative IOLs have also been proposed, which are based on the dynamic (multiple time) mechanical deformation of the shape of the lens, of the distance between two lenses (composing the IOL) and also some non-mechanical (electrically variable) lenses. In an article entitled "Accommodating IOLs: Emerging Concepts and Designs" published July 2004 in Cataract & Refractive Surgery Today, Samuel Masket MD describes such lenses and difficulties in characterizing a crystalline lens in situ, which is subject to forces exerted by adjoining tissues, leading to an inability to create an implant having desired properties under forces exerted by adjoining tissues postoperatively.

The tunable liquid crystal lens (TLCL) technology is an emerging technology that is suitable for IOL applications. The present applicant, LensVector, manufactures a TLCL product as detailed at http://lensvector.com/wp-content/uploads/2014/04/Gen3-Product-Brief-V1.pdf.

SUMMARY

In accordance with the proposed solution an implantable optical system allowing dynamic adaptation of its operation to the above mentioned environmental changes is provided. The implantable optical system provides for repeated remote programming without removing the implant while providing aberration adjustment.

In accordance with an aspect of the present proposed solution a biocompatible intraocular lens prosthesis is provided configured to fit within a capsular bag of an eye from which a natural eye lens is removed.

In accordance with a further aspect of the proposed solution a reprogrammable intraocular implant apparatus for replacing a natural lens of an eye is provided. The apparatus includes an encapsulated tunable liquid crystal optical device and a substantially transparent encapsulating material configured to provide a fixed optical power element for augmenting the optical power of the tunable liquid crystal lens. The encapsulating material can form a pronounced lenticular shape at least over: an accommodation clear aperture of the tunable liquid crystal lens. The encapsulating material can encapsulate the drive signal generator, driver, controller, power storage and a sensor component arranged about the periphery of said tunable liquid crystal lens. The encapsulated tunable liquid crystal optical device includes: a variable optical power tunable liquid crystal lens having a segmented hole patterned electrode, the tunable liquid crystal lens having an accommodation clear aperture; a tunable liquid crystal lens drive signal generator configured to generate a plurality of drive signals components, each drive signal component being configured to drive a corresponding hole patterned electrode segment; a tunable liquid crystal lens driver configured to control the drive signal generator to change the tunable liquid crystal lens optical power in response to a stimulus signal; a remote re-programmable tunable liquid crystal lens controller configured to set at least one hole patterned electrode segment's bias parameters to compensate for dynamic adaptation of the eye over time; power store configured to store electrical power to drive the tunable liquid crystal lens, the driver and the controller; and a sensor component configured to provide the stimulus signal.

In accordance with a further aspect of the proposed solution there is provided an intraocular implant apparatus for replacing a natural lens of an eye, the apparatus comprising: an encapsulated tunable liquid crystal optical device including: a tunable liquid crystal lens having a variable optical power having an accommodation clear aperture; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal; and a transparent encapsulating material configured to provide a fixed optical power element for augmenting said optical power of said tunable liquid crystal lens, said encapsulating material forming a pronounced lenticular shape at least over said accommodation clear aperture of the tunable liquid crystal lens, said encapsulating material encapsulating said drive signal generator, tunable liquid crystal lens controller, said power storage and said sensor component arranged about the periphery of said tunable liquid crystal lens.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having an optical power varying between a negative optical power and a positive optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal.

In accordance with a further aspect of the proposed solution there is provided an intraocular implant apparatus for replacing a natural lens of an eye, the apparatus comprising: an encapsulated tunable liquid crystal optical device including: a bipolar tunable liquid crystal lens having a variable optical power; a tunable liquid crystal lens drive signal generator configured to generate at least one drive signal component to drive said tunable liquid crystal lens; a tunable liquid crystal lens controller configured to control said drive signal generator to change said tunable liquid crystal lens optical power in response to a stimulus signal; a power store configured to store electrical power to drive said tunable liquid crystal lens and said controller; and a sensor component configured to provide said stimulus signal in response to a stimulus external to said optical device.

The variable optical power tunable liquid crystal lens can use a variety of different control electrode configurations, as for example one of: an inner ring electrode within an aperture of the hole patterned electrode, a segmented inner ring electrode within the aperture of the hole patterned electrode, a floating electrode, a pattern of concentric capacitive rings within the aperture of the hole patterned electrode, and a pattern of segmented concentric capacitive rings within the aperture of the hole patterned electrode.

In some embodiments, there is provided a method of reprogramming an implanted intraocular lens implant apparatus replacing a natural lens of an eye. The method comprises measuring an optical transfer function of the implanted eye. This intraocular lens implant has a variable optical power tunable liquid crystal lens with at least one segmented hole patterned electrode and a tunable liquid crystal lens drive signal generator configured to generate a plurality of drive signals components, each drive signal component being configured to drive a corresponding hole patterned electrode segment. The measured optical transfer function is compared with an ideal optical transfer function of the implanted eye. A variable optical power tunable liquid crystal lens controller of the implanted intraocular lens implant is recalibrated to adjust at least one of: the optical transfer function, at least one hole patterned electrode segment's bias parameter and a drive signal phase to compensate for dynamic adaptation of the eye over time.

In some embodiments, measuring the optical transfer function comprises employing one of a refractometer and an abberometer to determine the optical transfer function of the eye. Recalibrating the tunable liquid crystal lens controller can comprise adjusting at least one of: the optical transfer function, at least one hole patterned electrode segment's bias parameter and a drive signal phase to compensate for dynamic adaptation of the eye over time. Recalibrating the tunable liquid crystal lens controller can comprise one of: transmitting at least one adjustment to the tunable liquid crystal lens controller and identifying an eye gesture to select an adjustment of the tunable liquid crystal lens controller.

BRIEF DESCRIPTION OF THE DRAWINGS

The invention will be better understood by way of the following detailed description of embodiments of the proposed solution with reference to the appended drawings, in which:

FIG. 7 is a schematic diagram illustrating a distribution of liquid crystal molecular orientations during bipolar operation of a tunable liquid crystal lens in accordance with the proposed solution;

FIG. 8A is schematic diagram illustrating an encapsulated tunable liquid crystal lens in accordance with the proposed solution;

FIG. 8B is schematic diagram illustrating an encapsulated tunable liquid crystal lens having a fixed optical power positive lens element deposited thereon in accordance with the proposed solution;

FIG. 8C is schematic diagram illustrating an encapsulated tunable liquid crystal lens having a fixed optical power negative lens element deposited thereon in accordance with the proposed solution;

FIG. 19A is a schematic diagram illustrating a polarization dependent tunable liquid crystal lens layered structure of an intraocular device having a variable conductivity layer geometry in accordance with the proposed solution;

FIG. 20 is a schematic diagram illustrating a layered structure of a polarization dependent TLCL of an intraocular device having a split cell geometry in accordance with the proposed solution;

DETAILED DESCRIPTION

Overview

Figure 1:
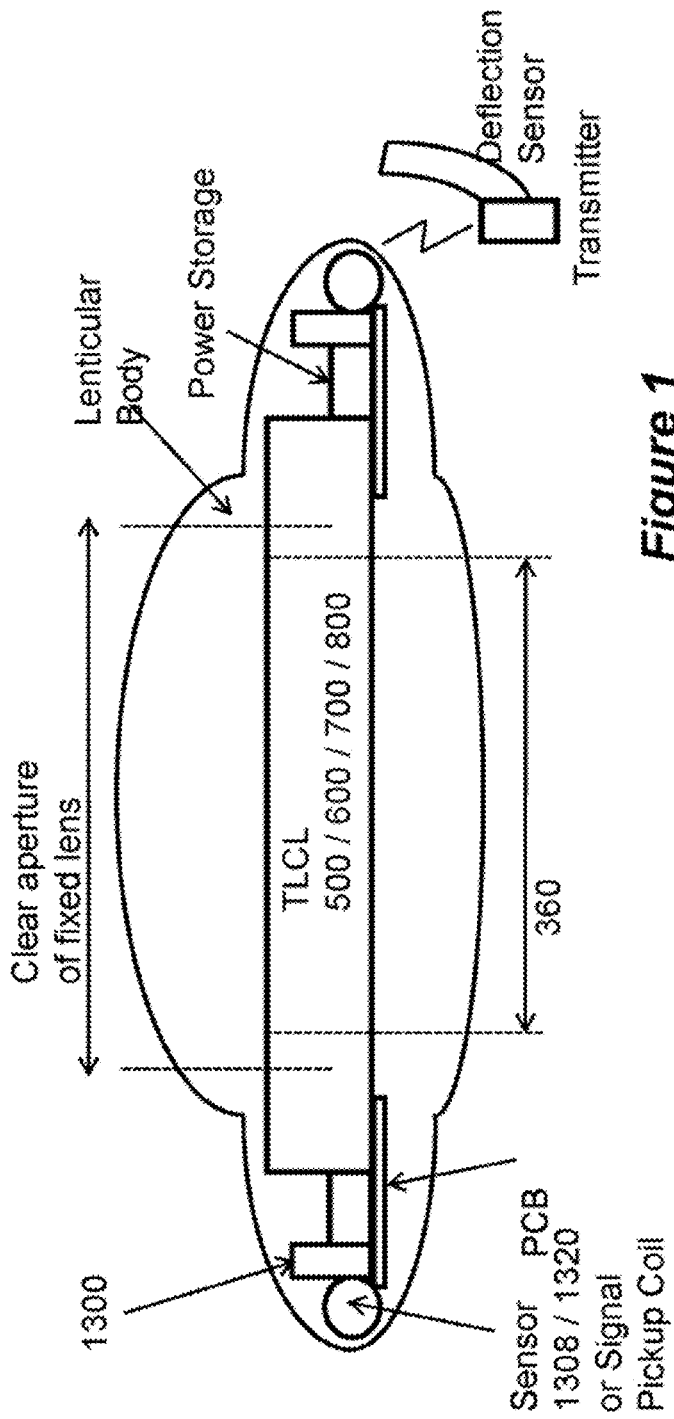
FIG. 1 is a schematic diagram illustrating a cross-section through an integral encapsulated tunable liquid crystal lens intraocular prosthesis in accordance with the proposed solution.
Figure 3:
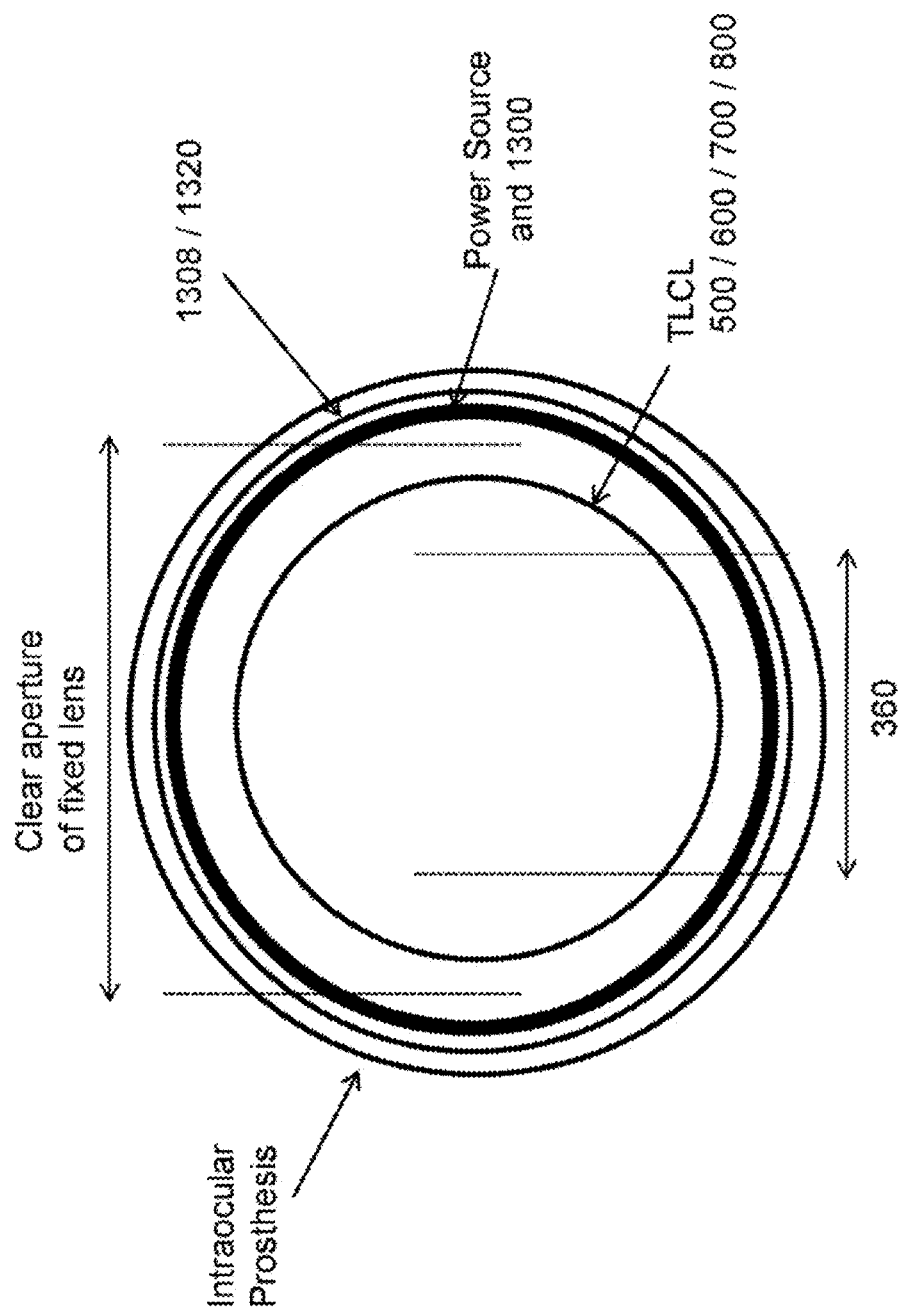
FIG. 3 is a schematic diagram illustrating a top view of an integral encapsulated tunable liquid crystal lens intraocular prosthesis in accordance with the proposed solution.

A schematic illustration of an intraocular implant is shown in FIG. 1. The TLCL device contained within the implant normally has two layers of liquid crystal arranged to variably focus light of both linear polarizations, although four layers (see FIG. 6) can be provided for better optical properties (optical power and image uniformity). As schematically illustrated in FIG. 3, electronic components are contained in a border portion of the implant, and the TLCL has its aperture within the aperture of the fixed lens of the implant.

Figure 14A:
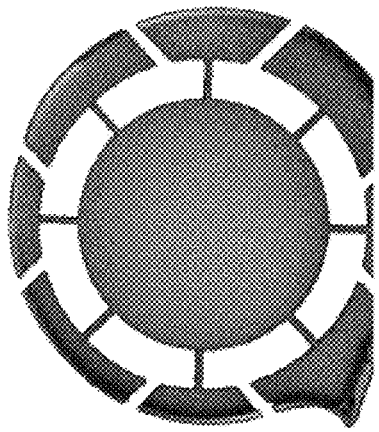
FIGS. 14A, 14B and 14C are illustrations showing fringe patterns corresponding to increasing optical power in a parametric TLCL in accordance with the proposed solution.

The TLCL has a control electrode that is made of a number of segments, as can be understood from FIG. 14A, where an example with 8 segments is shown. Such a TLCL allows for the gradient index lens to be configured by setting the relative electrical signals to each electrode segment in a manner that allows the position of the optical axis and the shape of the lens to be defined within certain limits. Vision errors, such as astigmatism for example, can be corrected by providing suitable offsets or bias parameters to the control signals. See the examples of FIGS. 16 and 17 where astigmatism and coma corrections are illustrated.

Figure 4A:
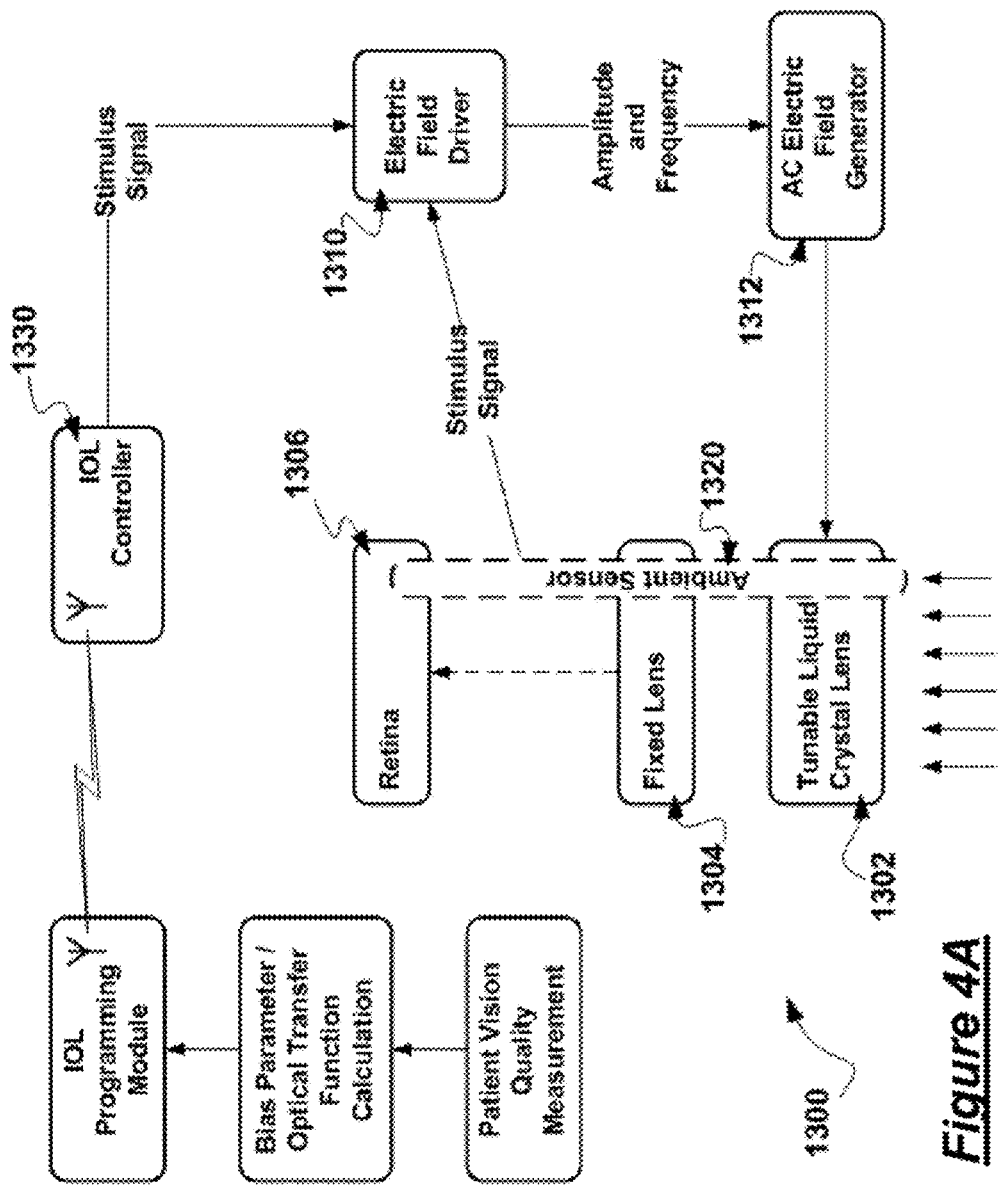
FIG. 4A is a schematic functional diagram showing interconnected tunable liquid crystal lens control components of an optical system and collocated components providing assisted focus adjustment functionality in accordance with the proposed solution.

As described above, it is known that intraocular implants provide an improvement to patient vision, however, the correction can fall short of the fully desired correction either immediately following surgery or with time. As illustrated schematically in FIG. 4A, a system is shown that includes patient vision quality measurement apparatus, such as a refractometer and/or an abberometer. This is instrumentation known in the art, and used clinically by optometrists and ophthalmologist to measure vision quality in patients. The desired correction for the IOL can be calculated using a bias parameter or optical transfer function calculator, as shown in FIG. 4A. This device can be implemented in a computer using a user interface at which the eye-care professional inputs the patent vision quality data, or as illustrated in the figure, it can receive data automatically from the vision quality measurement equipment.

There are essentially two options for determining the offset or bias parameters for controlling the electrode segment signals. This determination can be done within the IOL or externally. In the external option, the external device is configured to calculate the required parameters for the specific IOL design or model, and either in the bias parameter or optical transfer function calculator itself or in the IOL programming module, the specific offset parameters are calculated for the specific implant. The IOL programming module transfers the required data to the IOL controller 1330 and the driver 1310 will then operate to control the signal generator 1312 to provide electrode segment signal that correct vision for the patient as desired. In the "within the IOL" option, the optical transfer function desired can be transmitted from the IOL programming module to the controller 1330, and the controller 1330 can interpret the desired optical transfer function to determine the desired parameters in driver 1310. In both options, driver 1310 drives the electrode segments of TLCL 1302 with the appropriately adjusted control signals to correct vision while adjusting for accommodation.

In FIG. 4A, the stimulus signal is illustrated as being communicated from the controller 1330 to the driver 1310. In this configuration, the external IOL programming module is configured to control the focus setting of the IOL during calibration without relying on patient-based triggers for adjusting the focus. This can accelerate and make more accurate the calibration process. In this way, the calibration parameters transmitted to the implant and implement by the implant can be measured immediately using the patient vision quality measurement equipment to see if they are effective. Adjustments to the calibration parameters can be iteratively performed until the eye-care professional is satisfied that the best calibration has been achieved, and for all accommodations of the TLCL, namely at least for near vision accommodation, and optionally for all optical powers used by the implant of the TLCL.

Full TLCL

For operation in natural lighting conditions, two cross-oriented LC cells are required to control light propagation for two orthogonal polarizations of incident light (Sun, lamp) to provide a polarization independent TLCL.

PCT Patent Application WO/2009/153764, which is incorporated herein by reference, describes two orthogonally oriented liquid crystal layers arranged, respectively, above and below a common, middle ring electrode, which is coated by a single high resistivity material used to control both LC layers. The single middle electrode is intended to provide a spatially modulated electric field for both the upper LC layer and the lower LC layer with each of the two layers acting on a different polarization direction of light. The spatial profile of the electric field (and thus the optical power) was shown to be the same for both the upper and lower layers. In manufacturing, the lower LC layer has the middle electrode placed on top of it, and the upper LC layer is either fabricated on top of the middle electrode or separately fabricated and then bonded to the lower LC layer/middle electrode combination.

Figure 5A:
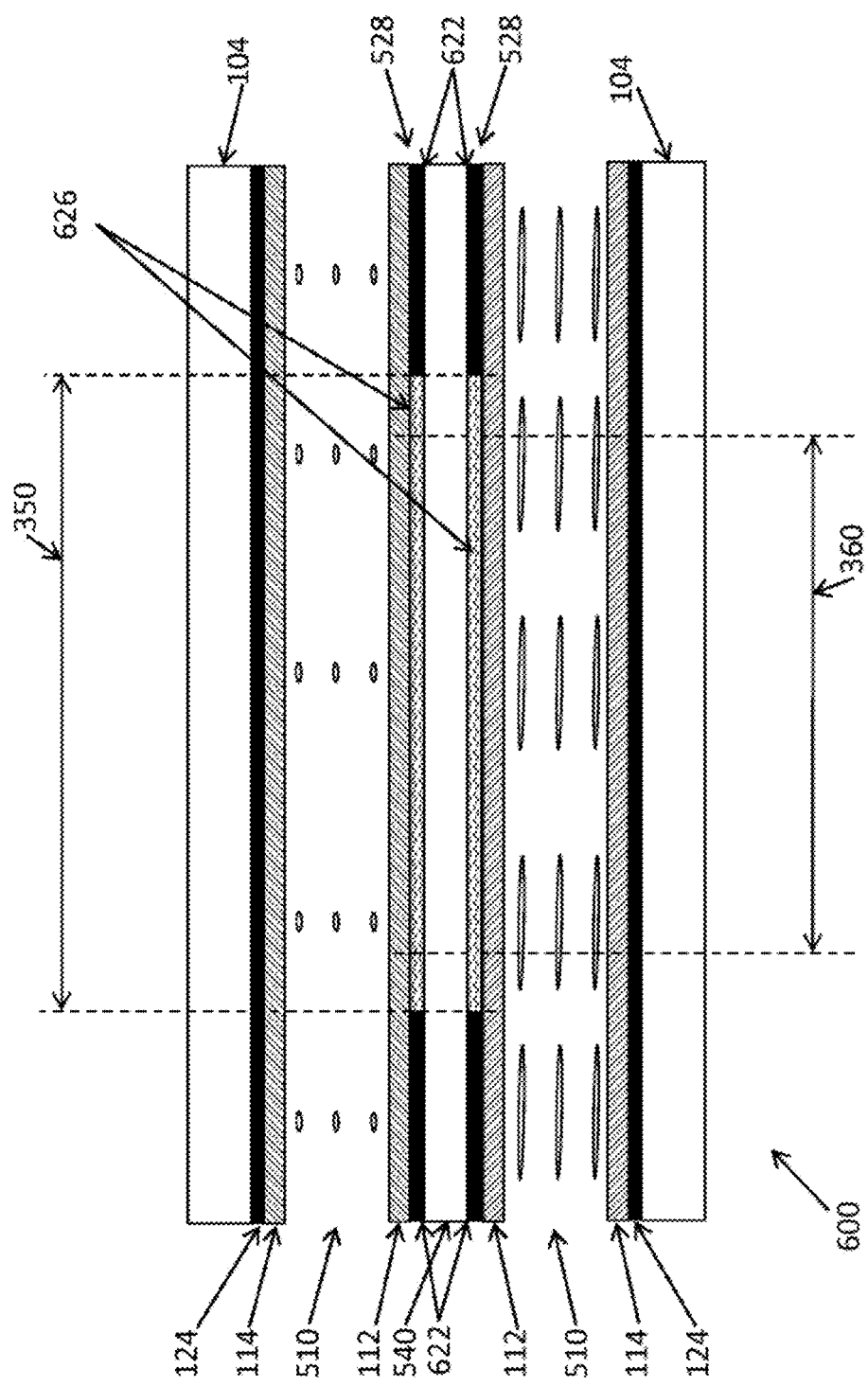
FIG. 5A is a schematic representation of a polarization independent liquid crystal lens which combines two of the cells of arranged with alignment layers at 90 degrees to each other and the weakly conductive layers.
Figure 5B:
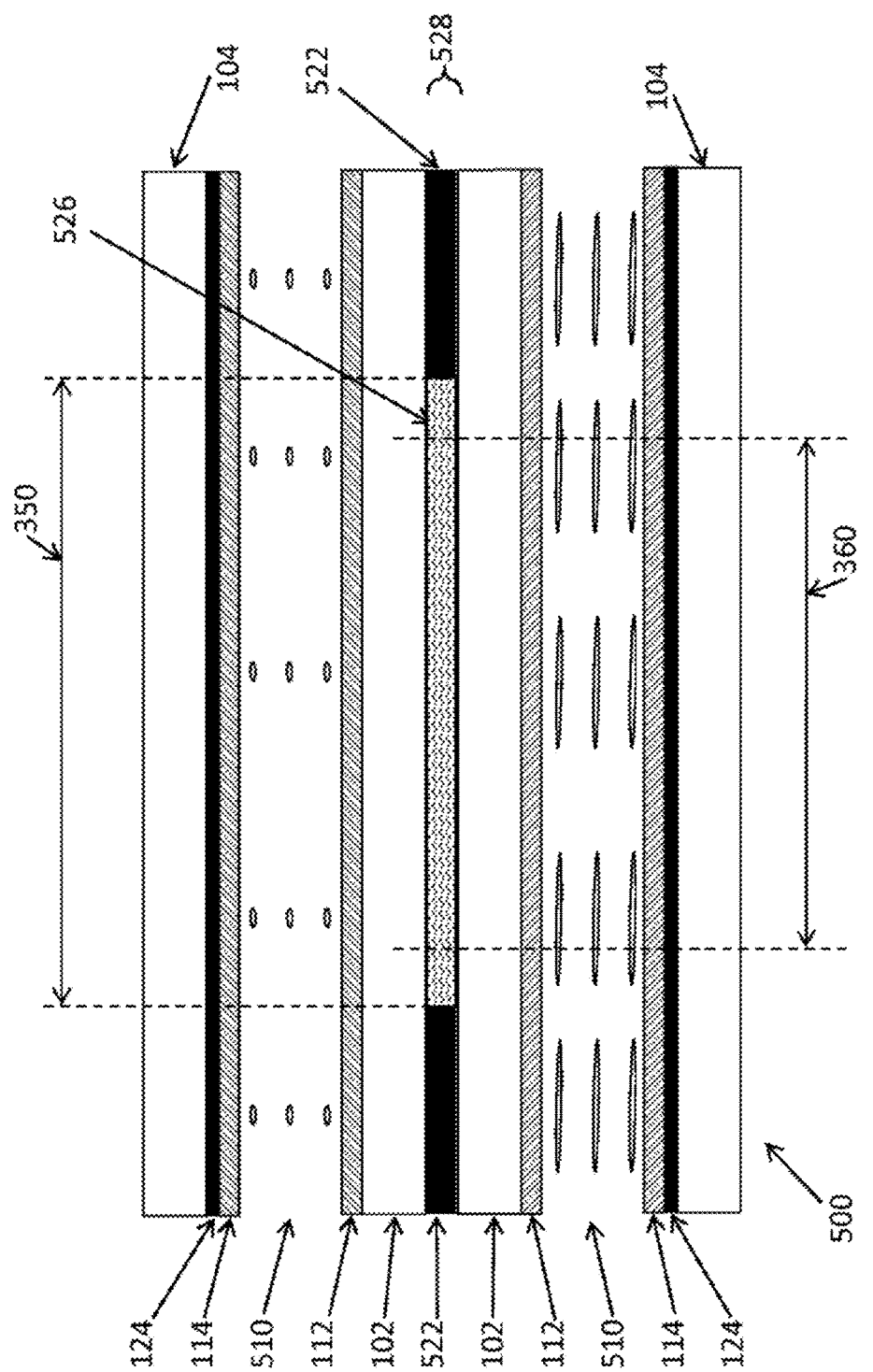
FIG. 5B is a schematic diagram illustrating a polarization independent tunable liquid crystal lens layered structure having a common variable conductivity layer in accordance with the proposed solution.

Without limiting the invention, illustrated in FIG. 5B is a polarization independent TLCL controlling the propagation of light passing therethrough including a common variable conductivity layer employing only one weakly conductive layer for controlling two liquid crystal cells. Preferably a polarization independent tunable liquid crystal lens intraocular prosthesis is configured to control light propagation for two orthogonally polarized incident light beam components, for example employing a mirrored TLCL structure.

With reference to FIG. 5B, TLCL structure 500 has a frequency dependent variable conductivity layer 528 including a common hole-patterned mid conductive electrode 522 forming an aperture 350 and a common frequency dependent weakly conductive layer 526 filling the aperture in the center of the common hole-patterned electrode 522. The frequency dependent variable conductivity structure is shared. Respective top and bottom substrates 102 can be optionally configured to provide buffering. Remaining layers are present substantially in mirror fashion about the mid variable conductivity layer shown bearing similar labels according to the functionality provided (qualified by top and bottom identifiers herein below). The central variable conductivity layer is positioned between two LC layers 510. Electrodes 124, to which the drive signal is provided, are located, respectively, adjacent to each LC layer 510, away from the central variable conductivity layer and therefore away from the common hole-patterned conductive electrode 522.

With reference to FIGS. 5A and 5B, each one of the two liquid crystal layers 510 employed may be said to have a different LC director orientation as do aligning coatings 112 and 114. Preferably, the two LC layers 510 have directors in substantially orthogonal planes. For example, with the normal of the TLCL layered structure 500 designated as the Z axis, one of the directors might be in the XZ plane while the second director being in the YZ plane.

In commonly-assigned international patent application PCT/IB2009/052658, the specification of which is hereby incorporated by reference, a Tuneable Liquid Crystal Lens (TLCL) is disclosed for which an electric field created by a ring electrode placed close to a uniform electrode is shaped in a desired manner. This TLCL cell is well-suited to being combined with another similar cell.

Illustrated in FIG. 5A is an embodiment in which two TLCL cells 510 are joined together. This combination of two polarization dependent TLCLs illustrates the presence of two hole patterned electrodes 522 which allows each half TLCL to be driven independently. The use of two such hole patterned electrodes 522 is optional, and a single hole patterned electrode 522 can be sufficient for operation as described herein.

The second half TLCL of the structure illustrated in FIG. 5A is essentially the same as the first, however having its liquid crystal molecules oriented to act on a polarization of light orthogonal to that of the first cell. The two cells of the FIG. 5A embodiment provide focusing for each of two orthogonal polarizations. An electric field for controlling the lower LC 510 of the lower cell is developed between the lower hole patterned electrode 622 and the bottom electrode 124, in conjunction with lower WCL 626. Control of the LC 510 of the upper cell, however, makes use of the top hole patterned electrode 622 and top WCL 626 of the upper cell, which develop the electric field for controlling the top LC 510 along with the top planar electrode 124.

It will be appreciated by those skilled in the art that using a single control signal drive circuit for two cells (FIG. 5A) can be advantageous over using separate control signal sources for independent cells (FIG. 5B) in that the necessary number of layers and control signals is reduced. However, when independent control over the cells (FIG. 5A) is desired, there is still an advantage to achieve better control.

The invention is not limited to the LC lens layered structures illustrated herein, while distinct WCL layers are shown, when reference is made to a WCL herein after, such reference is defined to include sheet resistance dominated materials, variable conductivity, frequency dependent characteristic materials for example described in the above mentioned PCT application PCT/IB2009/052658, and in International Patent Application PCT/CA2011/050651 filed 14 Oct. 2011 entitled "In-Flight Auto Focus Method and System for Tunable Liquid Crystal Optical Element" claiming priority from U.S. Provisional Patent Application 61/424,946 filed Dec. 20, 2010, both of which are incorporated herein by reference.

For ease of description of the following TLCL functionality, an abstraction of control electrode structures providing spatial shaping of the driving electric field is made by referring to the electric field shaping control layer 428/528. In general frequency dependent structure is employed having a frequency dependence not only defined by the frequency dependent material in the weakly conductive layers but also by the structure of capacitance of the electric field shaping control layer 428/528 (in which the weakly conductive material plays important role of resistance) including the capacitance of conductive layers and that of the LC layer 510. The functionality described hereinbelow applies to other implementations of the proposed solution such as, but not limited to, those shown in FIG. 5A.

Tunable Optical Device System

In accordance with the proposed solution, the variable optical power response of a TLC lens is employed to create an intraocular TLCL prosthesis with variable optical power. Optical power can be varied between a minimum and a maximum by employing a mixed frequency and amplitude control responsive to a stimulus signal and at least one reprogrammable parameter.

With reference to FIG. 4A, the control drive signal for tuning the TLCL can be provided by control signal electronics 1300 configured to cause the TLCL to control light propagation as a function of at least one measured physiological change and/or at least one environmental condition. As an example, an intraocular TLCL control system is schematically illustrated in FIG. 4A to have a TLC lens 1302 optionally combined with at least one fixed lens element 1304 to focus an image onto retina 1306 of the eye with the TLC lens 1302 providing focus control. The perceived image either causes a measurable physiological change (1308), for example involuntary muscle tension, and/or a physiological change caused via a voluntary (conscious) act, for example lid movement, squinting, etc. A transducer 1308 is employed to detect the physiological change, for example a pressure, tensile, stress, etc. sensor can measure muscle compression, tension, deflection etc. It is appreciated that a ciliary muscle plays a part in natural accommodation and the physiological change transducer 1308 can be configured to monitor the ciliary muscle of the eye. However, the invention is not limited to measuring physiological changes in the ciliary muscle; a variety of muscles intraocular or external can be used, for example muscles associated with the eyelid. Transducer 1308 provides a stimulus signal. It is appreciated that physiological changes such as squinting can be involuntary for example induced by a light intensity change separate from scene changes. An ambient (external) sensor 1320, providing an additional stimulus, can be employed to augment/correct the stimulus signal provided by the transducer 1308 (for example to provide a weighting factor).

An electric field driver 1310 translates at least one stimulus into at least one electrical drive signal parameter. Without limiting the invention, the electric field driver 1310 can employ lookup tables in performing its overall function, or at least as such a translation function relates to taking into consideration empirical information regarding the TLC lens 1302 and the general optical system, including but not limited to external sensor stimuli. For an intraocular TLCL prosthesis replacing the natural lens, the external sensor can be configured to take into consideration the effect of the variable iris of the eye and/or the electric field driver 1310 can be configured to take into account typical time variant iris variability (for example time variant calibration curves can be employed via lookup tables). For example time variant natural iris variability information can be employed to adjust the response of the electric field driver 1310 to prevent positive feedback situations unnecessarily driving the TLCL lens to extremes. It is expected that the natural reaction of the natural iris (and the nervous system controlling the iris) is plastic and that the iris will also react to operational particulars of the TLCL intraocular implanted prosthesis. The ambient sensor 1320 is illustrated in FIG. 4A to be in the optical path, for example behind the iris. The invention is not limited to a TLCL intraocular prosthesis replacing the natural lens of the eye, implantation of a TLCL in other eye cavities places the TLCL either in front or behind the iris and therefore the location of the ambient sensor 1320 can be varied accordingly. As another example, the physiological change sensor 1308 and/or ambient sensor 1320 can be replaced by an image sensor pointed towards the retina of the eye and receiving backscattered light from the retina. With only a limited number of pixels, such a sensor can be configured to detect sharpness in an image projected onto the retina, the image sensor proving a focus score as a stimulus signal.

An electric field drive generator 1312 converts the electrical drive signal parameters into at least one drive signal to be applied to the TLCL 1302. Those skilled in the art would appreciate that component 1310, without limiting the invention, can be implemented using microcode executed on a microcontroller, while component 1312 can include voltage sources switched under the control of a microcontroller to provide a resulting drive signal of desired frequencies and RMS voltages. Such a microcontroller can be configured to obtain stimuli and determine drive signal parameters to operate the TLCL 1302 to change optical power towards best focus. For example best focus can be asserted by detecting minimal stimulus signal change below a threshold.

Frequency signal generators are known, and only limited details are provided herein with respect to employing such a frequency signal generator to implement a TLCL control component of a tunable optical system. For example, in order to provide low power operation, a miniature frequency generator can include a voltage boost circuit and an "H" bridge circuit having several (4) MOSFETs. The power consumption of such a circuit is estimated using typical efficiency numbers from commercially available components and found not to violate operational parameters for an intraocular prosthesis. The power dissipated by the MOSFET switches have three components; static power, dynamic power and load power. Static power is the sum of all biasing components. Dynamic power is the charge and discharge of the MOSFET gate capacitance and the load power is the power dissipated across the MOSFET's drain and source terminals (Imax*RDS(on)). Assuming the availability of a low voltage power source for controlling drive signal amplitude, voltage can be boosted by either using a switched capacitor ("charge pump") circuit or an inductive circuit. In either case the efficiencies for commercially available products are found to be similar and within operational parameters. Inductive boost offers some advantages over the charge pump.

In accordance with the proposed solution, there is provided an intraocular lens controller 1330 configured to control the operation of the electric field driver 1310. The intraocular lens controller 1330 is reprogrammable and includes a remote programming interface via which electric field driver 1310 parameters can be changed. For example an ophthalmologist or optometrist can, over the remote programming interface, interrogate the electric field driver 1310 for operational parameters and/or set the operational parameters. The interrogation can be automatic without requiring human intervention beyond initiating it at the appropriate time. In some implementations the intraocular lens controller 1330 programming interface has a dedicated antenna, in other implementations the programming interface shares an existing antenna on the intraocular device for example with an ambient sensor pickup coil or with recharge electronics. In yet other implementations re-programming the intraocular lens controller 1330 can involve eye gestures as described herein. Re-programming of the intraocular lens controller 1330 enables long term and repeated adaptation of the intraocular device to account for eye aging, plasticity, uneven healing, etc. effects experienced post operatively. Such adjustments can be rewritten with subsequent programming:

Use Example

In use, an eye-care professional, such as an optometrist or ophthalmologist can employ different techniques to perform at least one vision quality measurement (FIGS. 4A and 4B) for example such as, but not limited to, using a refractometer to determine low order aberrations of the eye. Performing such vision quality measurements can be automatic without requiring human intervention (beyond initiating thereof at the appropriate time). Using a refractometer on the natural eye lens slated for removal provides information about the physiology of the overall eye with the intent to determine low order aberrations such as a predominant optical power required for comfortable vision. Based on the low order aberration information, an intraocular TLC lens prosthesis can be selected, possibly including a base optical power, based on a combination of the index of refraction and curvature of the lenticular body(ies) for example illustrated in FIG. 3A, possibly also including a fixed optical power element, for example as illustrated in FIGS. 8B and 8C. The intent of the selection is to provide comfortable unaided vision using the intraocular prosthesis in an unpowered state, for example comfortable far vision, comfortable vision at an arm's length or comfortable vision at a reading distance which can depend on the TLCL 600/700/800 employed. As an example, the TLCL geometry can be manufactured to require fixed optical power for a 20-20 vision eye prior to cataract surgery. The selection of the TLCL intraocular prosthesis can also take into account expected capsular bag deformation in the absence of the natural lens.

An ophthalmologist surgically implants the TLCL intraocular prosthesis, using methods beyond the scope of the present description. Such surgery can have been performed recently or some time previous to the calibration done herein, as the present embodiment also allows for recalibration over time as eye ages. Preferably the TLCL intraocular prosthesis is rolled or folded for insertion into the capsular bag through a small incision and allowed, or caused, to unfurl within the capsular bag. If the intraocular prosthesis is configured to also have a fixed optical element which compensates for base coma and/or astigmatism, the ophthalmologist would need to also correctly rotate the prosthesis. A surgical refractometer, or other suitable optical equipment, may be employed for the purpose. As is known in the art, it is important for the intraocular TLCL prosthesis to register with respect to the eye's optical axis irrespective of the correct rotational orientation mentioned.

Prior, during or post surgery, using an external intraocular lens prosthesis programming module (FIGS. 4A and 4B), the intraocular TLCL prosthesis is configured to correct visual aberrations of the eye. This can include programming an optical transfer function including voltages, frequencies and phase differences as required for the TLCL intraocular prosthesis to express the corrective wavefront correction. The programming at least provides a bias in terms of an RMS voltage, a frequency or a phase angle difference. For certainty, the programming can be automatic without requiring human intervention (beyond initiating it at the appropriate time).

A post surgery period is allowed for the eye to heal, seal the incision and allow the tissues of the eye to settle by which it is understood that the quasi final eye pressure and corneal tension is being exerted. The tissues of the eye are subject to tissue plasticity, as are the muscles of the eye which may have less of an effect on the prosthesis and therefore on the overall vision post surgery. Some muscle fibers may atrophy. Large vision variation can be experienced during the first month after surgery as the eye heals and gets used to the new norm. The long term state includes a low aging process past about a month from surgery.

Figure 4B:
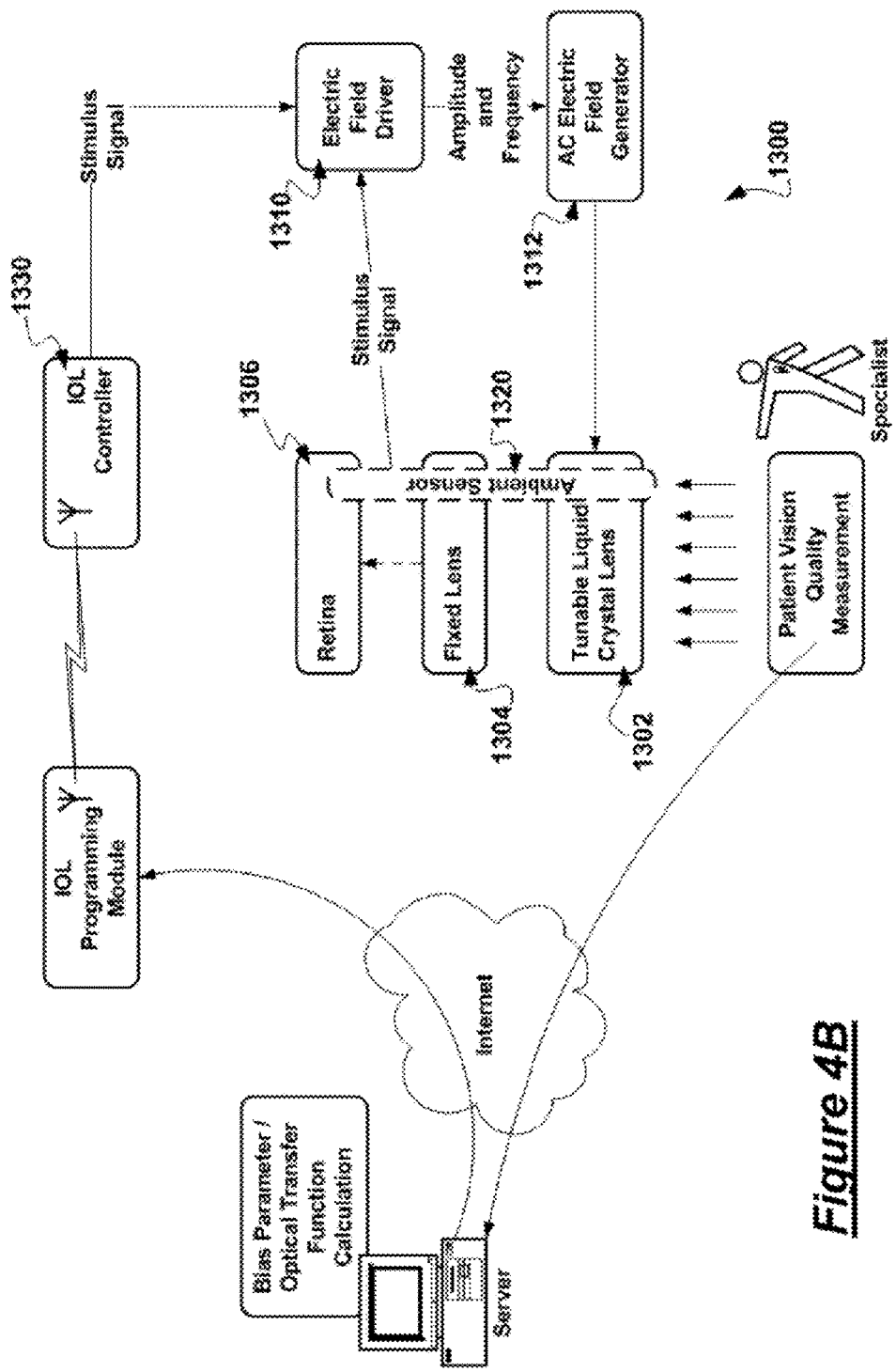
FIG. 4B is a schematic functional diagram showing interconnected tunable liquid crystal lens control components of an optical system and remote components providing assisted focus adjustment functionality in accordance with the proposed solution.

Depending on the indicated recovery regimen, one or more re-programming of the TLCL intraocular prosthesis can be performed. In accordance with a use example, a patient vision quality measurement is performed employing Shack-Hartmann aberrometry, or a suitable vision field test (FIGS. 4A and 4B). Such vision quality measurement can be automated without requiring human intervention (beyond initiating thereof at the appropriate time). The results of the vision quality measurement are employed to calculate the post operative optical transfer function of the TLCL intraocular prosthesis aided eye. In one implementation illustrated in FIG. 4A the calculation is performed (automatically) locally in the specialist's office, in another implementation illustrated in FIG. 4B the calculation is performed remotely, for example on a dedicated server adapted to address higher order eye aberrations. For example the remote server can be interrogated with a patient personalized code to obtain optimized TLCL configuration parameters to aid in reprogramming.

The post operative optical transfer function of the aided eye can be compared (automatically) (FIGS. 4A and 4B) with the ideal optical transfer function and differences determined. The comparison and determination, via associated calculations (FIGS. 4A and 4B), provides for example one of a drive signal bias parameter, a drive signal phase difference or an entire optical transfer function. The ophthalmology professional can then initiate reprogramming the TLCL intraocular prosthesis either by loading an entire optical transfer function via the remote programming interface or individual programming parameters of the TLCL intraocular prosthesis can be adjusted without removing or replacing the TLCL intraocular prosthesis. For certainty, reprogramming is only limited by the performance limits of the TLCL intraocular implanted prosthesis and the prescribed eye vision correcting regimen. After the first few months post surgery, the TLCL intraocular prosthesis can be further reprogrammed to account for aging effects of the eye without removing or replacing the TLCL intraocular prosthesis. Without limiting the invention, reprogramming can be automated without involving human intervention (beyond initiating thereof at the appropriate time).

In accordance with another use example, the TLCL intraocular prosthesis implanted patient is presented with various eye vision charts as is well known in the art to determine the visual acuity of the implanted eye. The TLCL intraocular prosthesis can be set in a programming mode remotely and a programming instructions card can be exchanged with the eye chart. For example a programming card having a sequence of numbered dots/lines in a pattern can be used to adjust the TLCL intraocular prosthesis via eye gestures following the pattern on the card. As a simple example a programming card having an "A-frame" pattern can be employed to increase a currently adjusted parameter (optical power, degree of astigmatism, degree of coma), conversely a "V" shaped pattern can be employed to decrease the currently adjusted parameter. Chevron "<" and ">" patterns can be employed to cycle through the adjustable parameters, while "=", "X", "/" and "\" patterns can be employed accept, reject, drill down with respect to a parameter tree or return to more generic parameters. For certainty, the invention is not limited to any particular eye gesture or set of gestures.

Implementations of Intraocular TLCL Prostheses

Figure 6:
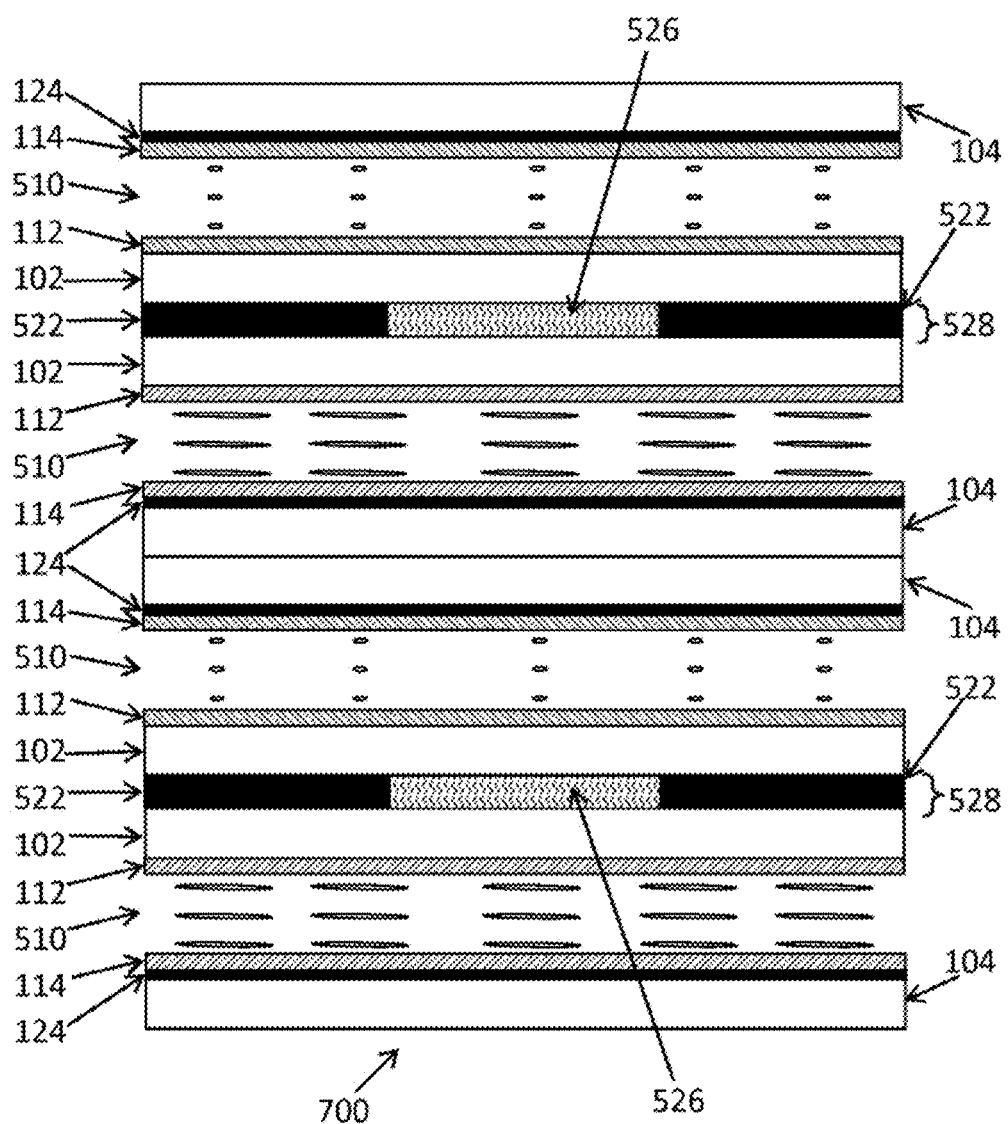
FIG. 6 is a schematic diagram illustrating a dual full tunable liquid crystal lens structure in accordance with the proposed solution.

By way of a non-limiting example and with reference to FIG. 5A for a full TLCL, with reference to FIG. 6 for dual full TLCL 700 and with reference to FIG. 7 for bipolar full TLCL 800, the geometry of an intraocular variable optical power flat TLC lens implemented in accordance with the proposed solution are provided. Suitable biocompatible/non-toxic materials have been tested and are assumed in the following. Thermal cycling tests confirm long term storage and have shown compatibility with sterilization requirements while retaining operability. Experimental tests have shown long life times measured in years. It will be appreciated that TLCL intraocular optical devices can be fabricated using layer-by-layer assembly and, preferably, in a parallel way (many units simultaneously, called "wafer level"), the final product being obtained by singulation and, optionally, joining single TLCLs with operation axes (directors) in cross (orthogonal) directions to focus both orthogonal polarizations of light into full TLCLs. While TLCLs configured in accordance with the above disclosure exceed the required operational parameters of an intraocular TLCL prosthesis, it will be appreciated that miniaturization and low power operability of such TLCLs in an adaptive intraocular prosthesis is subject to greatly varying dimensions depending on geometry, choice of materials, and particularly depending on tradeoffs between operational parameters:

The typical available capsular bag size following natural lens removal is about 9 mm in diameter and 4 mm in thickness (anterior to posterior dimension). FIG. 5A/5B illustrates a 0.5 mm thick flat full TLCL 500/600, FIG. 6 illustrates a 1 mm flat dual full TLCL 700 while FIG. 7 illustrates a 0.5 mm thick flat bipolar TLCL 800 employing 100 µm glass substrates 124. For example, TLCLs having an accommodative clear aperture 360 of about 4.5 mm can provide at least 1.7 diopters employing a single flat full TLCL 500/600, at least 3.5 diopters employing a dual flat full TLCL 700, and at least 7 diopters employing a flat bipolar full TLCL 800. A 4.5 mm accommodative clear aperture 360 benefits from relatively small incisions. Larger accommodative clear apertures 360 while permitting operation in lower light conditions would require larger incisions and/or foldable TLCL structure however at reduced optical power. For example a 6 mm accommodative clear aperture 360 would provide roughly half the optical power of a TLCL having 4.5 mm accommodative clear aperture 360. Even at 6 mm accommodative clear aperture, sufficient structural material reserve around the clear aperture 350 can be provided to ensure operability without violating capsular bag dimensions. Conversely, smaller accommodative clear apertures 360 benefit from requiring smaller incisions and operation at higher optical powers. For example, TLCLs having an accommodative clear aperture 360 of about 3 mm can provide at least 3.5 diopters employing a single flat full TLCL 500/600, at least 7 diopters employing a dual flat full TLCL 700, and at least 14 diopters employing a flat bipolar full TLCL 800 providing greater coverage of the juvenile accommodation range. Smaller accommodative clear apertures 360 while providing increased optical power can restrict light throughput. Light throughput can be increased by expanding light transmittance of the TLCL structure layers and/or that of any encapsulating material. For example, employing more flexible thinner single full TLCL 500/600 or single bipolar full TLCL 800 allows at least 90% transmittance. Less flexible thicker dual full TLCL 700 allows at least 80% transmittance. Reducing the thickness of some layers can change (reduce/increase) transmittance depending on material/physical properties of the layer material.

Assuming a 20-20 vision prior to removal of a natural lens for example during a cataract operation in an adult, an optical power range of 3 diopters, while limited compared to the juvenile accommodation range, typically can provide sufficient optical power variability to permit a focus range spanning from infinity to about 30 cm. An optical power range greater than 3 diopters can provide closer focus and/or increased ability to correct imperfect vision. For example, 2.5 diopters can be useful for correcting presbyopia. Thus depending the visual condition which is to be addressed, different adaptive accommodation is required and therefore different optical range variability is required. It will be appreciated that some spare optical power is useful to account for other factors.

For example, the (dual) full TLCL structure (700) 500/600 can be configured to focus at infinity employing maximum optical power and at a closest focusing distance employing minimum optical power. Depending on whether the TLCL is configured as a positive lens or a negative lens, infinity focus or closest focus can correspond to maximum power drive or minimum power drive. The configuration may depend on factors such as focusing ability of the eye prior to surgery, selected mode of driving the TLCL, etc. Alternatively, without limiting the invention, employing a bipolar TLCL 800 infinity focus can be provided by driving the TLCL at maximum optical power of one polarity, closest focus can be provided by driving the TLCL at maximum optical power of the other polarity, and focus at a working/reading distance/arm's length can be provided employing zero optical power adjustment.

Top and bottom alignment layers 112/114 can include Polyimide layers about 20 nm thick that are rubbed to yield surfaces which induce a liquid crystal ground state alignment with a low pre-tilt angle, for example 3°. For example, the liquid crystal layer 510 can be 5 to 30 µm thick, with larger thicknesses providing greater optical power. Thicker liquid crystal layers 510 tend to require higher operating temperatures and drive signal power.

The hole-patterned electrode 322 can be made of an opaque metal such as Aluminum (Al), or it can be made of Indium Tin Oxide (ITO) which is transparent. The thickness of the hole-patterned electrode 322 can be about 10 nm. Without limiting the invention, the hole-patterned electrode layer 322 can also be substantially optically hidden and thus would not interfere with the propagation of light through the optical device.

The weakly conductive layer 426 can have a thickness of about 10 nm. The frequency dependent (permitivity or complex dielectric) material of the WCL 426 can comprise a variety of materials such as, but not limited to, titanium oxide. Titanium oxide has semiconductor properties that change with applied drive signal frequency.

In the embodiment of FIG. 5B, a hole-patterned electrode 522 and frequency dependent material 526 form a single variable conductivity layer 528 shared between two LC layers 510 reducing thickness.

Substrates 124 include a degree of flexibility permitting the TLCL 500/600/700 to bend and thus an incision of reduced size. The above assume 100 µm thick glass substrates. Greater flexibility can be achieved in dual TLCL structures by eliminating one of the central glass substrates 124 see, FIG. 6, or by employing thinner substrates 124. Substrates 124 can be as thin as 50 µm which combined with compliant (pliable) adhesives can provide a useful amount of flexibility and reduce incision size. Alternatively, incision size can be further reduced by employing a flat TLCL 500/600/700/800 having a circular outer shape. While typical TLCLs are wafer level manufactured and singulated employing standard scribe and dicing techniques into individual squares, laser cutting techniques have been successfully tested to singulate circular intraocular TLCLs.

Alternatively, the flat (dual) full TLCL structure (700) 500/600 can be encapsulated in a lenticular body which represents the intraocular prosthesis. A lenticular body of a substantially spheroidal outer shape can be employed as illustrated in FIG. 8A. It is appreciated that the natural lens and capsular bag are not necessarily symmetric.

If the natural eye prior to natural lens removal is not 20-20, then a baseline correction can be provided by employing a combination of a lenticular body shape configured to have a composition and an index of refraction. FIGS. 8B and 8C illustrate encapsulated TLCLs having additional fixed optical power lens elements (non-tunable) deposited thereon. Either or both flat surfaces the TLCL can have a fixed optical element deposited thereon. A combination of the lenticular body and fixed optical power elements can be employed to shift or amplify accommodation range of the intraocular prosthesis. For example, if the fixed optical element provides +11 diopters and if the TLCL provides an accommodation of 7 diopters (positive TLCL), then the optical power provided by such an intraocular TLCL prosthesis can change from 11 to 18 diopters. If a negative TLCL provides −7 diopters of accommodation, then the optical power provided by such an intraocular TLCL prosthesis can change from 11 to 4 diopters.

Figure 9A:
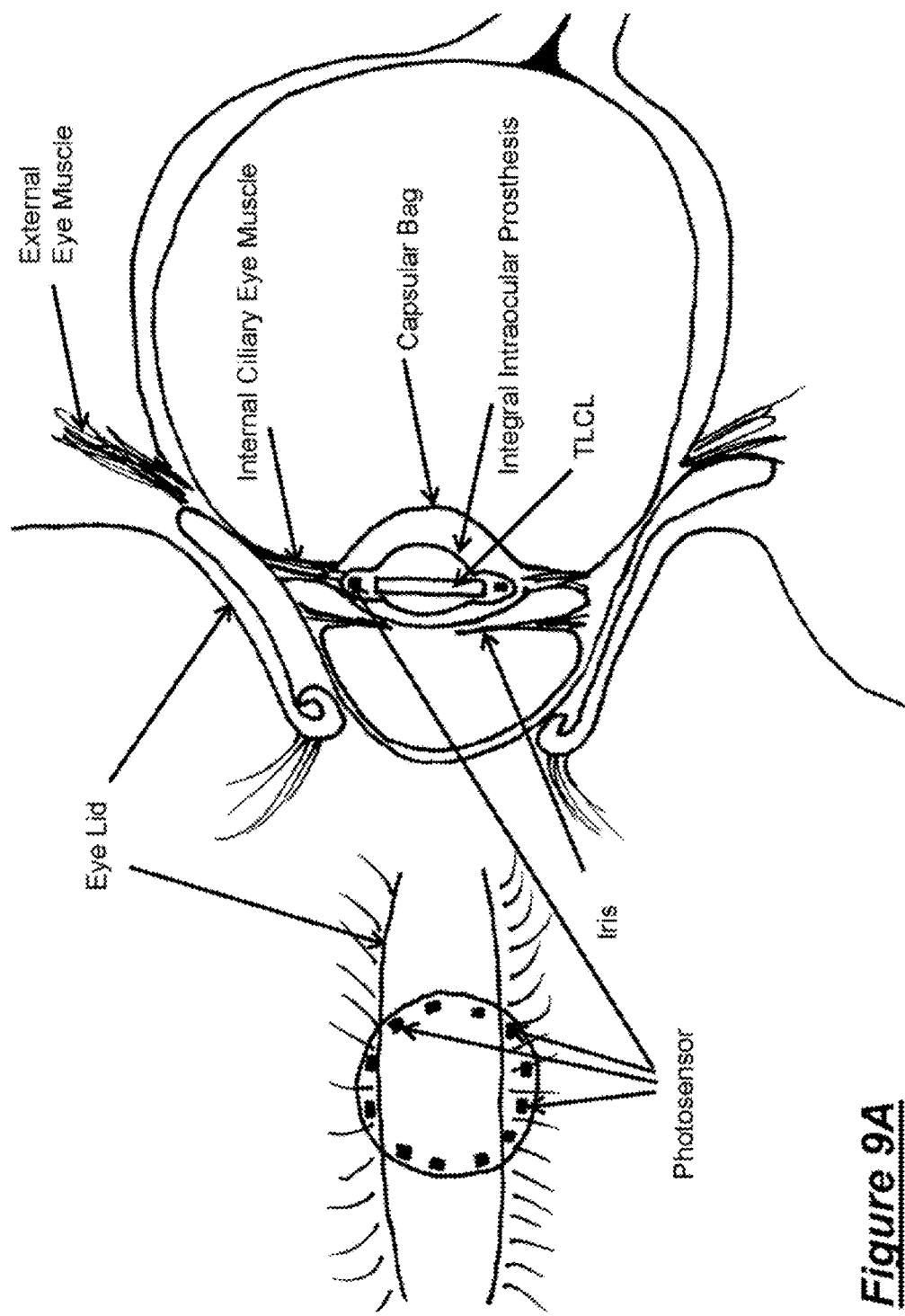
FIGS. 9A and 9B are schematic diagrams illustrating integral intraocular prostheses detecting physiological changes outside an eye.
Figure 9B:
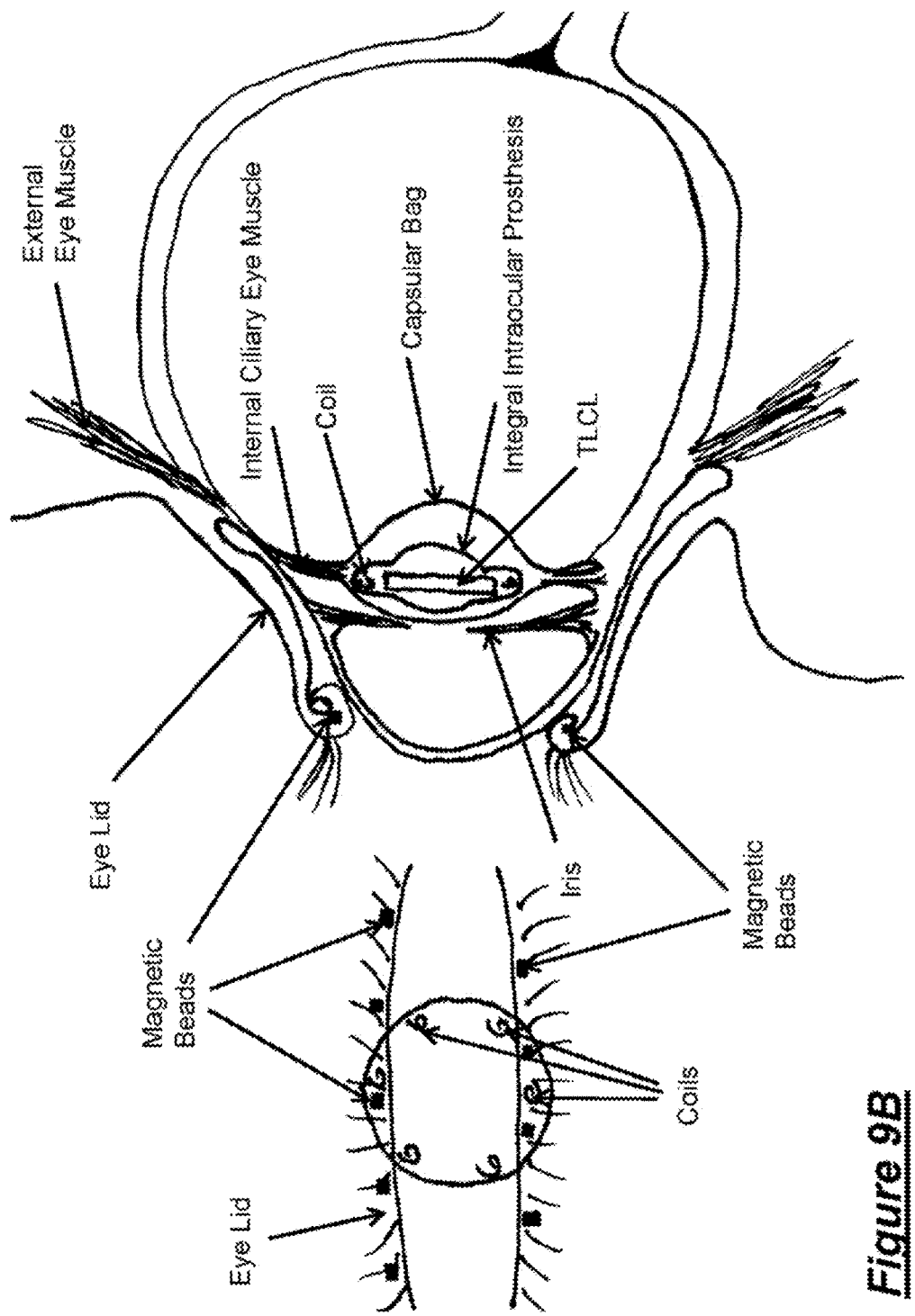

The position of the TLCL 500/600/700/800 intraocular optical device in convergence space is apparent particularly with reference to FIGS. 9A and 9B wherein more optical elements are present forward, with respect to light incidence, of the TLCL 500/600/700/800 and wherein the TLCL 500/600/700/800 is the last or penultimate optical element in the stack. With reference to FIGS. 9A and 9B it will be appreciated that "optical elements in the stack" includes body tissues such as the cornea, aqueous humor, iris, an intraocular lens, etc. all forward (but not necessarily) of the TLCL 500/600/700/800.

Figure 2:
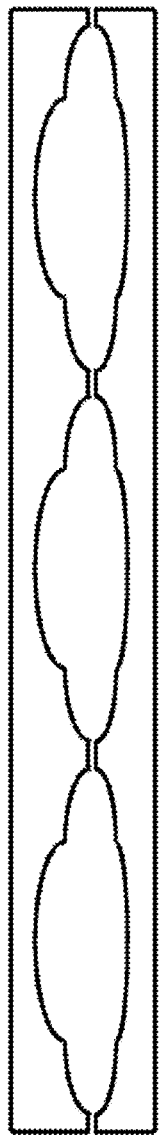
FIG. 2 is a schematic diagram illustrating a cross-section through a mold array for manufacturing encapsulated tunable liquid crystal lens intraocular prostheses in parallel in accordance with the proposed solution.

In accordance with some embodiments of the proposed solution, an integral intraocular prosthesis includes the TLCL 500/600/700/800, an electronics package 1300, and power storage on a flexible Printed Circuit Board (PCB), for example made of (biocompatible) Kapton™ (Kapton is a trademark of E. I. du Pont de Nemours and Company or its affiliates), the flexible PCB itself having a aperture. An example of such an integral intraocular prosthesis is illustrated in FIG. 1 to include encapsulating material forming a pronounced fixed optical power element over the TLCL and also encapsulating the electronics package 1300, and power storage component(s). It is understood that FIG. 1 is highly schematic, the lobed shape provides high optical power fixed optical lens elements by employing pronounced lenticular shapes. In accordance with another implementation of the proposed solution, FIG. 3 illustrates a top view of integral intraocular prosthesis showing the power source and electronics package 1300 being disposed around the periphery of the intraocular prosthesis. FIG. 2 illustrates a cross-sectional view of a mold for encapsulation during manufacturing of an array of intraocular TLCL prostheses. The mold includes an array of reservoirs for holding encapsulating material.

With the sensor 1308 being disposed around the periphery of the intraocular TLCL implant, such an internal pressure sensor can be configured to detect external mechanical action exerted onto the capsular bag, for example by the ciliary muscle.

Alternatively, an external deflection sensor and transmitter are illustrated in FIG. 1, external deflection sensor and transmitter which can be affixed to a muscle, not limited to the ciliary muscle, to measure physiological change in the form of muscle action and to transmit a stimulus signal to a pickup coil in the intraocular prosthesis. Muscles of the eyelid are other examples. Eyelid muscles have the advantage that they can be consciously controlled besides being autonomously/instinctively controlled by the body. For example the deflection sensor can include a piezo element. A number of piezo element arrangements can be configured to react to muscular bend, contraction, etc. to provide a feedback stimulus signal. Such piezo elements are compatible with any muscular environment in the vicinity of the eye including facial muscles about 1 cm away from the eye.

For certainty, external physiological change measurements do not necessarily have to be transmitted. FIGS. 9A and 9B (not anatomical) schematically illustrate integral intraocular prostheses detecting physiological changes outside the eye. Advantages are derived from a low power integral intraocular device.

In accordance with one implementation, sensor 1320 includes at least one, typically a number of, photosensor(s) disposed around the TLCL for detecting the position of the eyelid. FIG. 9A illustrates the location of the photosensors, the inset illustrates an example of a photosensor distribution around the integral intraocular TLCL prosthesis. The greater the accommodative clear aperture 360 employed, the more the photosensors 1308 spend time behind the iris for an intraocular TLCL prosthesis implanted in the capsular bag. The inset of FIG. 9A illustrates the relative position of the eyelid with respect to the photosensors during a blink or squint. A blink can be differentiated from a squint for example by low rate sampling which statistically miss a blink or by a relatively long term integration of light falling onto the photosensors. The position of the eyelid can be inferred from the pattern of light measurements. It can be appreciated that no additional procedure, aside from that replacing the natural eye lens with the integral intraocular TLCL prosthesis, is necessary in employing this implementation.

In accordance with another implementation of the proposed solution, the physiological change sensor 1308 includes at least one coil, typically a number of coils sensitive to varying magnetic fields. At least one magnetic bead, typically a number of magnetic beads, for example including niobium each, encapsulated in a biocompatible material can be implanted for example via injection into the rim of the eyelid as schematically illustrated in FIG. 9B. The human eye does not sit still moving involuntarily in random directions at a frequency in the range 30 to 70 times per second. The coil(s) can pick up magnetic field variations induced by both eyelid action and involuntary eye movement, and determine the degree of closure of the eyelid which can then be provided as a stimulus signal. Employing a number of magnetic beads the orientation of the eye within the eye socket can be taken into account.

In accordance with the proposed solution, in operation the stimulus signal is generated from measurements. For example, if the eyelid is closed then the TLCL lens is powered down; if the person is squinting then the TLCL is caused to focus at infinity (powered or unpowered), if not squinting/relaxed/opened up then TLCL is caused to provide high optical power (unpowered or powered). A variety of other eyelid gestures can be employed, without limiting the invention thereto.

In accordance with an implementation of the proposed solution, eyelid gestures may be distinguished therebetween and employed to operate the intraocular implant. For example, calibration can employ a test pattern at a particular distance from the eye employing eyelid gestures to accept/deny/increase/decrease/select/exit etc.

The power storage can include a battery or a capacitor. With respect to the power source, it would be appreciated that integral intraocular prostheses are limited to low power implementations. For example, a 5V battery or capacitor can be employed providing sufficient operational duration. For example, for a 3.0 mm accommodative clear aperture 360 implementation a full TLCL 500/600 would consume 0.035 mW while total power consumption, for both TLCL and electronics package 1300, is around 0.20 mW. A dual full TLCL 700 having a 4.5 mm accommodative clear aperture 360 would consume 0.157 mW with a total power consumption of about 1.35 mW. Lower power operation is possible as a tradeoff against other intraocular prosthesis operational parameters.

It is noted that the TLCL appears in an electrical circuit as a capacitive load. For example, at 7V/10 kHz operation, a full TLCL 500/600 having a 3.0 mm accommodative clear aperture 360 has a typical capacitance of about 70 pF, while a dual full TLCL 700 having a 4.5 mm accommodative clear aperture 360 has a typical capacitance of about 320 pF. Lower voltage operation is possible, however fast optical power transition times favor high voltage operation. For example, 7V operation can provide optical power transition times of about 0.4 s but can vary between 0.2 s and 0.6 s.

Functional Intraocular Prosthesis

Figure 10:
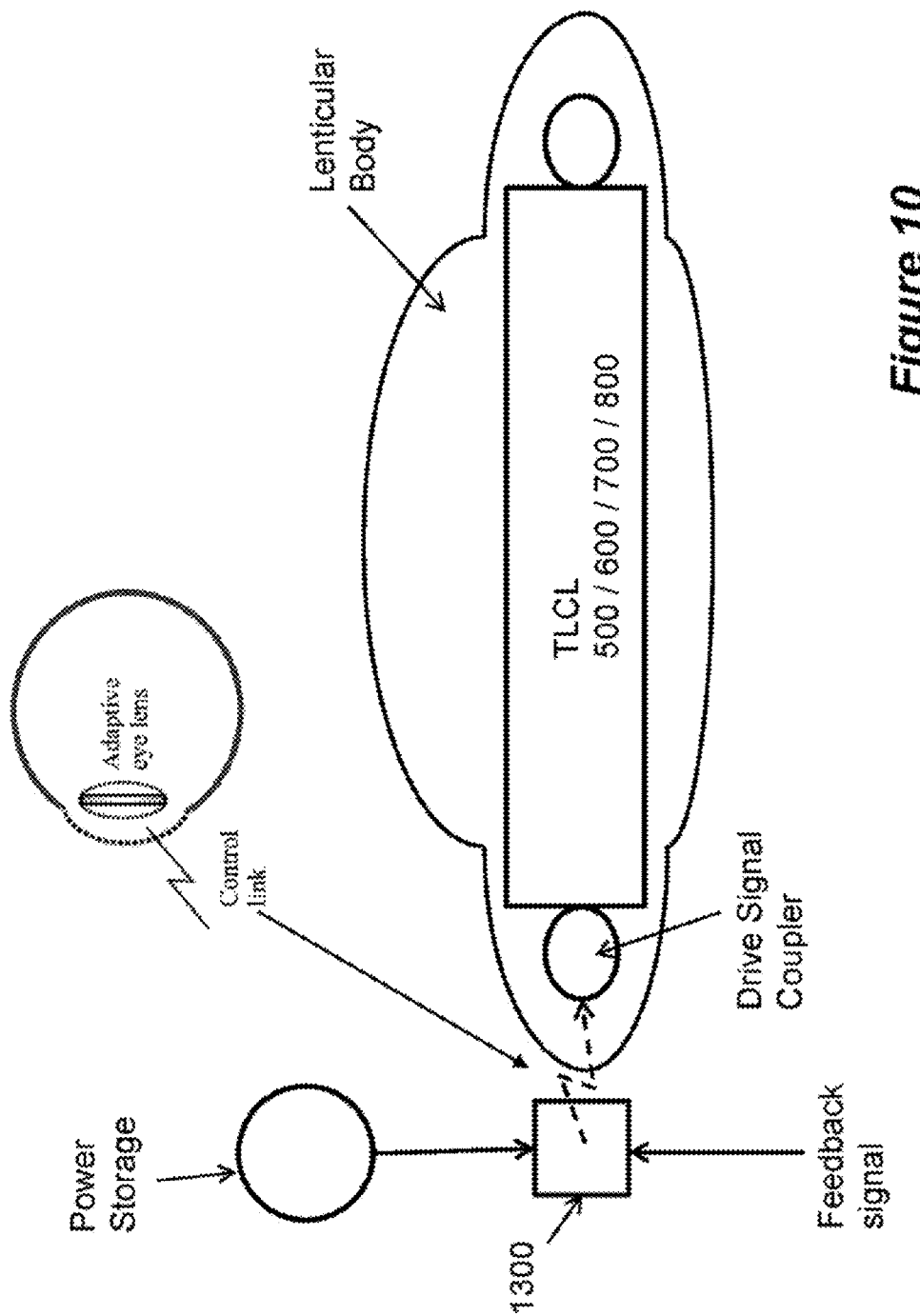
FIG. 10 is a schematic diagram illustrating an intraocular prosthesis having an external electronics package, the inset showing wireless control, in accordance with the proposed solution.
Figure 11:
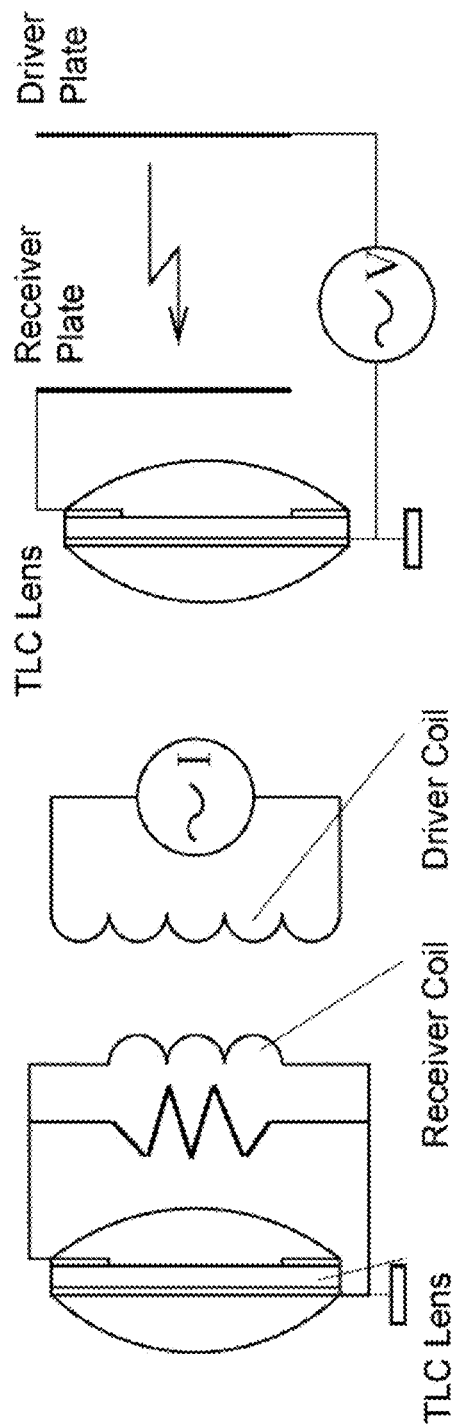
FIGS. 11A and 11B illustrate wireless inductive and capacitive drive respectively in accordance with the proposed solution.
Figure 12:
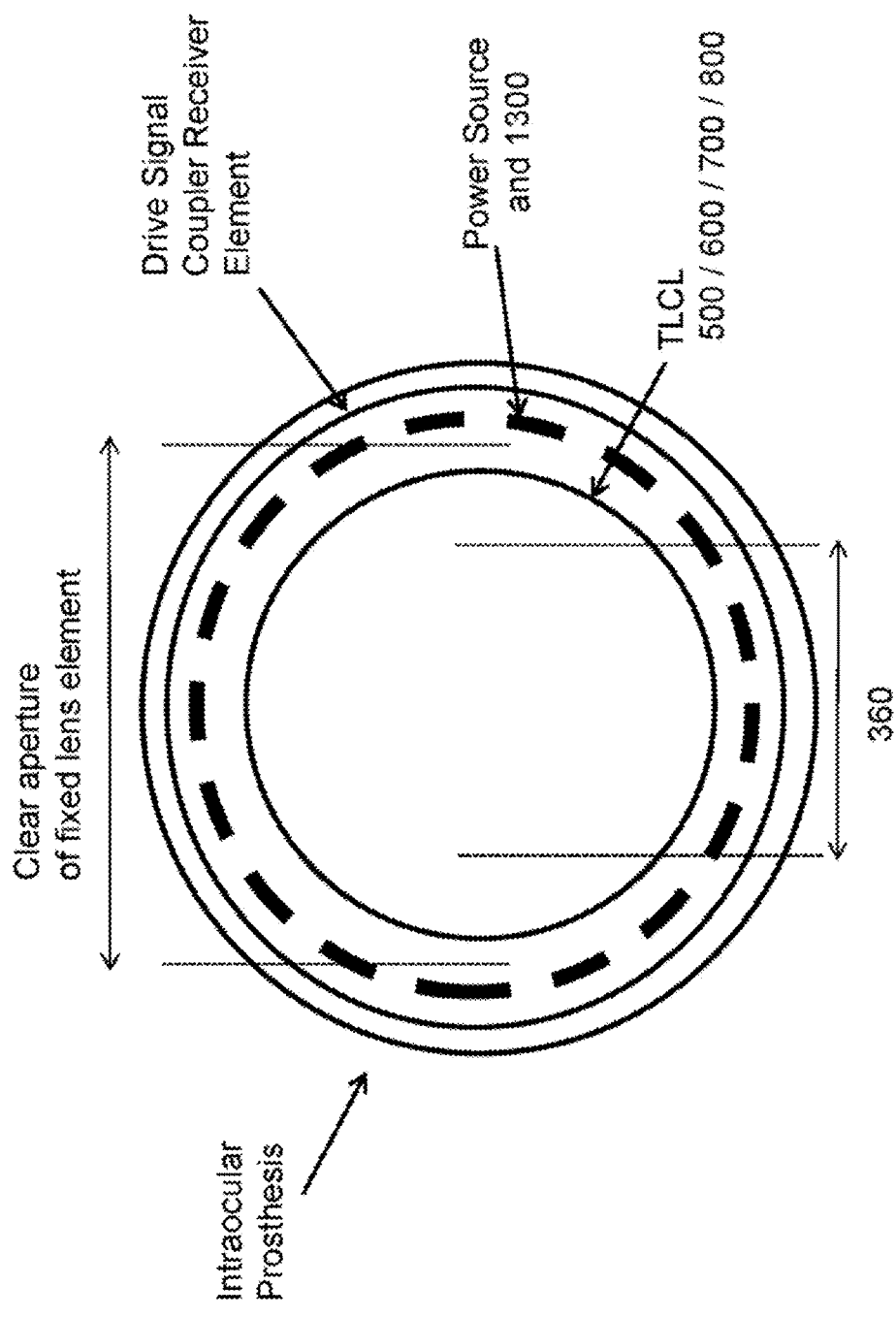
FIG. 12 is a schematic diagram illustrating the location of a drive signal receiver element of a drive signal coupler in accordance with the proposed solution.

FIG. 10 illustrates another implementation of the IOL wherein the electronics package is external, for example incorporated in an eye glasses frame (not shown). FIGS. 11A and 11B illustrate examples of wireless TLCL drive employing a drive signal coupler. FIG. 11A illustrates inductive drive coupling employed with the TLCL connected as a capacitor in an LRC resonant circuit. FIG. 11B illustrates capacitive drive coupling. It is understood that FIGS. 11A and 11B are electronic schematics: for certainty, the "receiver plate" in FIG. 11B need not be a component separate from the intraocular prosthesis and the fixed optical elements need not extend to the edges of the intraocular prosthesis. TLCL edges typically contain electrode layer contacts and require encapsulation. FIG. 12 illustrates the location of the integrated receiver coil/receiver plate of the drive signal coupler receiver element. It is understood that such a signal receiver element can also be used as a receiver element of a power coupler to recharge the power source (shown dashed) of an integral intraocular prosthesis or retard its depletion. For example, an eye glasses frame (including pianos) or an eye patch can be employed in a similar fashion as illustrated in FIG. 11A or 11B to recharge the power store (battery or capacitor) either during operation or at night. Such eye glasses frame or eye patch includes an external transmit element for transmitting power.

Particularly for purposes of initial or subsequent re-programming the signal coupler receiver element provides a physical programming interface for the intraocular lens device controller 1330, for example an antenna.

Parametric Intraocular Lens Device

The invention is not limited to the above description which assumes an aberration free eye, a perfectly manufactured intraocular prosthesis and on-optical axis placement of the intraocular lens device during the operation. While some of the liquid crystal cells described above, and illustrated in the drawings, have a hole-patterned annular ring electrode, the invention is not limited thereto. For example, International PCT Application PCT/CA2010/002023 filed Dec. 23, 2010, which is incorporated herein by reference, describes tunable liquid crystal optical devices, including but not limited to lenses, having a segmented hole-patterned electrode for controlling the electric field across the liquid crystal layer enabling asymmetric phase profiles to be applied for light tilting, optical image stabilization and sub-pixel shift capability. With feedback from an image sensor, such geometry can be used for image stabilization.

Figure 13:
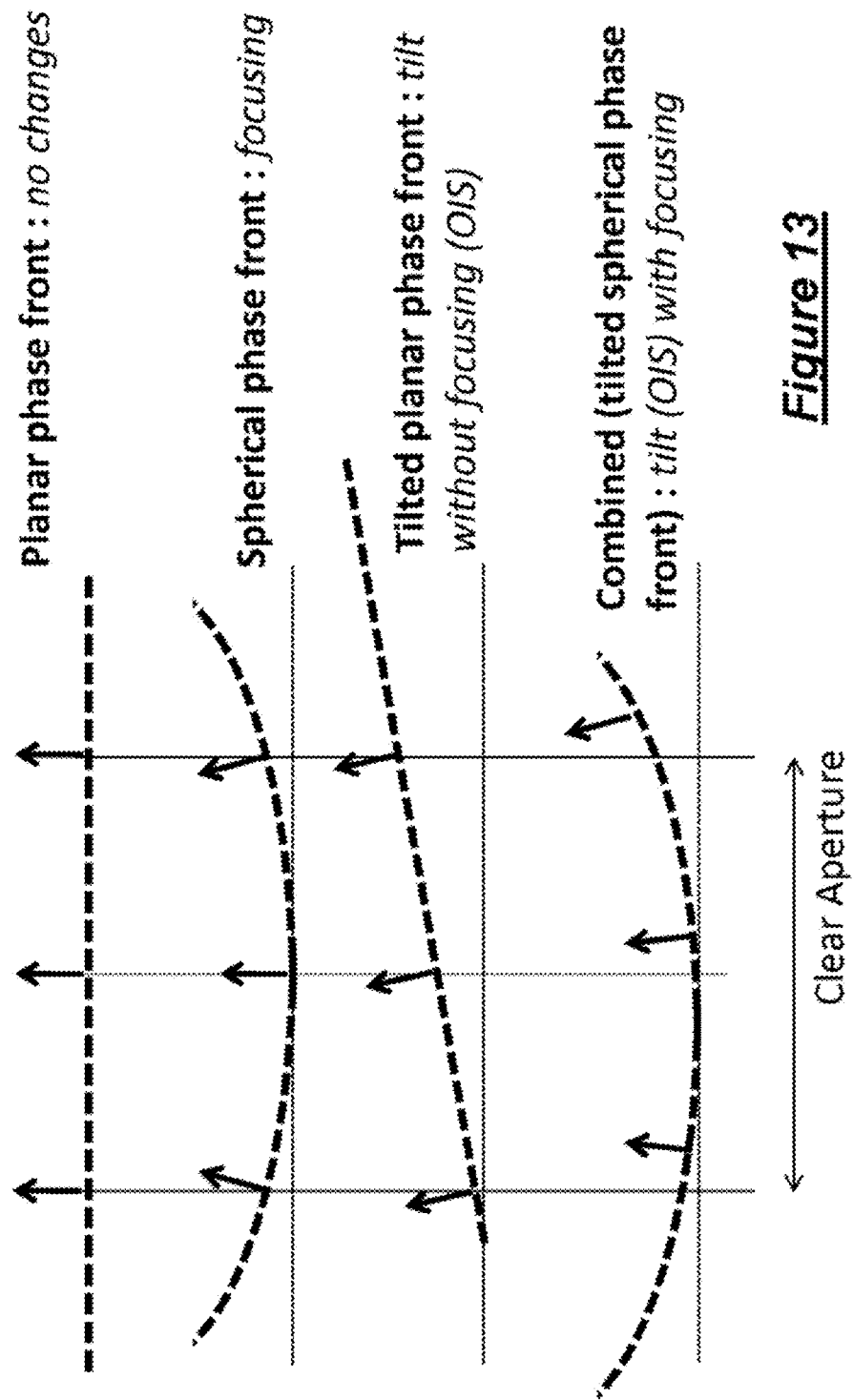
FIG. 13 is a schematic diagram illustrating wavefront correction for countering aberrations in accordance with the proposed solution.

With reference to FIG. 13, optical error correction of aberrations, astigmatism, coma, manufacturing errors, assembly errors, etc. can also be implemented in an integral intraocular prosthesis employing a parametric TLCL structure having segmented hole patterned electrodes. For example Tunable Liquid Crystal Lenses having a movable optical axis are described in co-pending, commonly assigned, International Patent Application PCT/CA/2010/002023 entitled "Image Stabilization and Shifting in a Liquid Crystal Lens" claiming priority from U.S. Provisional Patent Application 61/289,995 entitled "Image Stabilization and Shifting in a Liquid Crystal Lens" filed Dec. 13, 2009, the entireties of which are incorporated herein by reference. U.S. Patent Application publication US 2012/0113318 entitled "Methods of Adjustment Free Manufacture of Focus Free Camera Modules" filed 1 Nov. 2011, which is incorporated herein by reference, describes accounting for overall optical system optical error/aberration during TLCL manufacture.

Figure 14B:
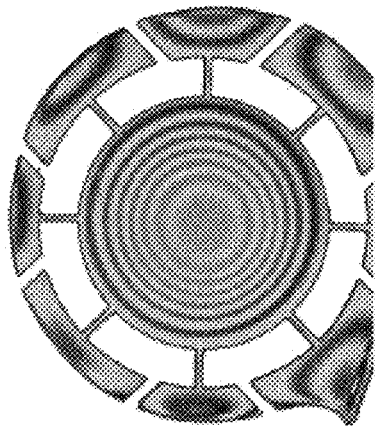
Figure 14C:
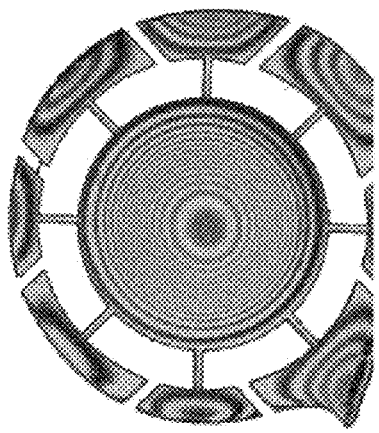
Figure 15B:
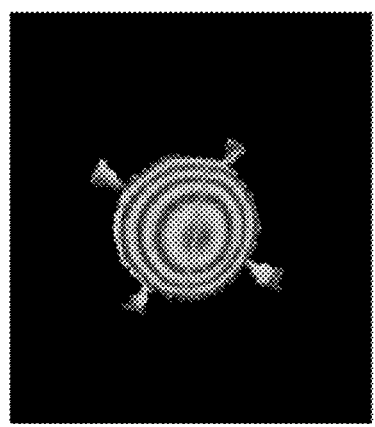
FIGS. 15A, 15B and 15C are illustrations respectively showing a left parametric shift, unshifted and right parametric shift employing a parametric TLCL in accordance with the proposed solution.
Figure 15A:
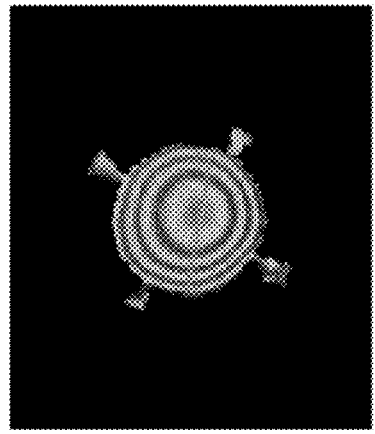
Figure 15C:
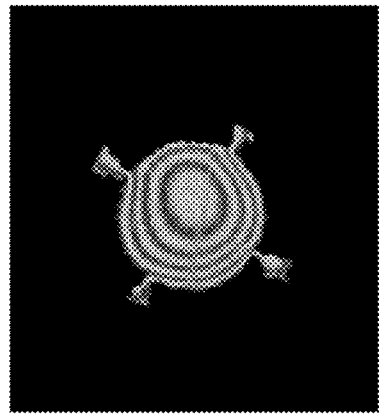
Figures 16, 17:
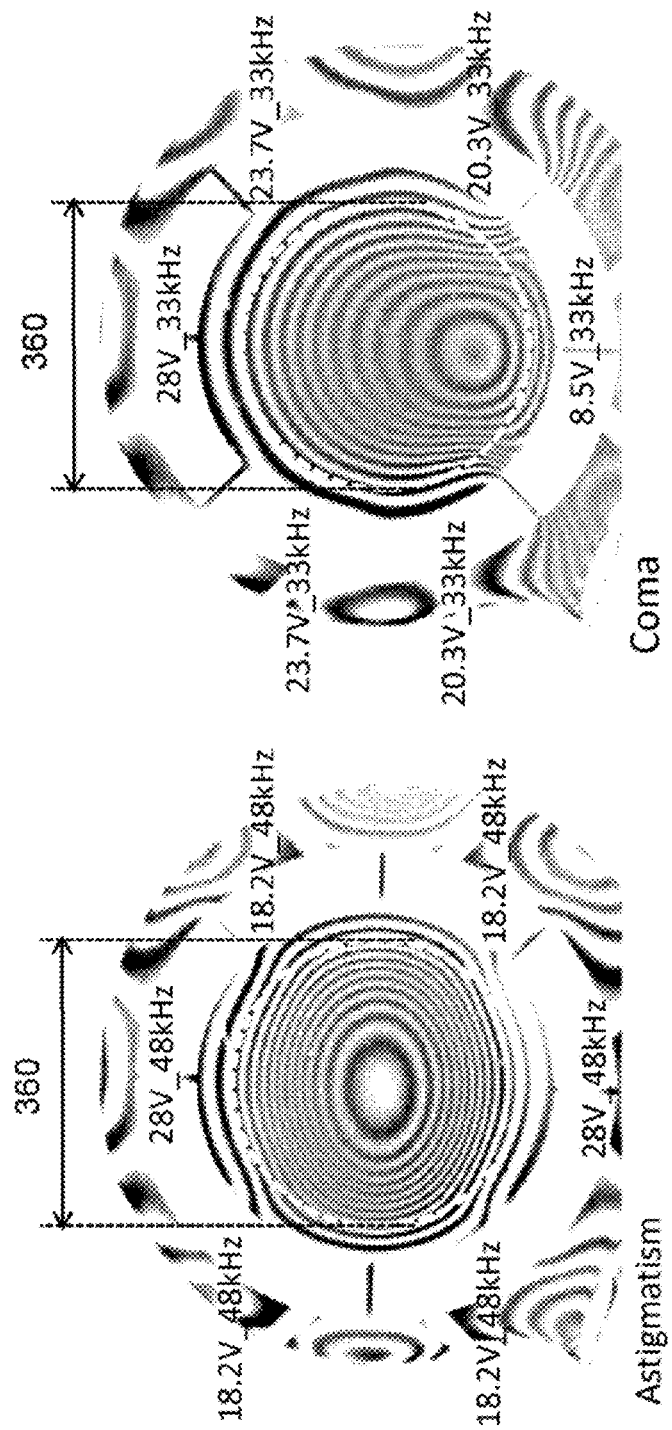
FIG. 16 is an illustration showing a fringe pattern of a parametric TLCL configured to correct an astigmatism aberration in accordance with the proposed solution.
FIG. 17 is an illustration showing a fringe pattern of a parametric TLCL configured to correct a coma error in accordance with the proposed solution.
Figure 18:
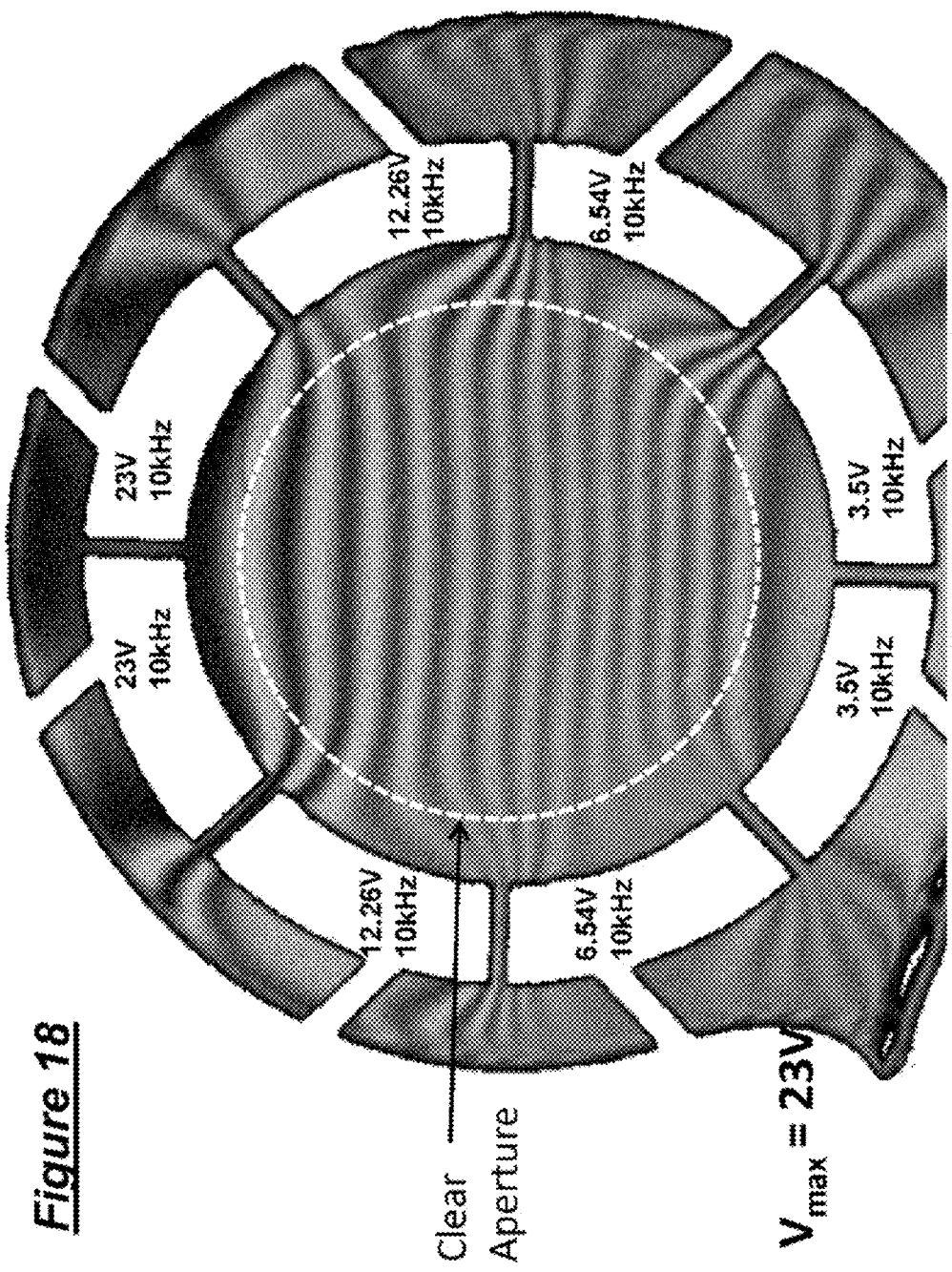
FIG. 18 is an illustration showing a fringe pattern of a parametric TLCL configured to correct a misalignment error in accordance with the proposed solution.

FIGS. 14A, 14B and 14C illustrate fringe patterns of a parametric TLCL having a segmented hole patterned electrode wherein the electrode segments are driven such that the TLC lens has 0 diopters (FIG. 14A), medium (FIG. 14B) and high (FIG. 14C) optical power. FIG. 15A illustrates a fringe pattern of a TLCL focusing an incident light beam with an optical power. FIGS. 15B and 15C illustrate left and right parametric shifts. In accordance with the proposed solution, FIG. 16 illustrates a fringe pattern of a TLCL intraocular lens device configured to correct astigmatism aberrations while FIG. 17 illustrates a fringe pattern of a TLCL intraocular lens device configured to correct comma aberrations. FIG. 18 illustrates a fringe pattern of a parametric TLCL intraocular lens device configured to correct for misalignment errors in implanting the intraocular lens device.

Figure 19B:
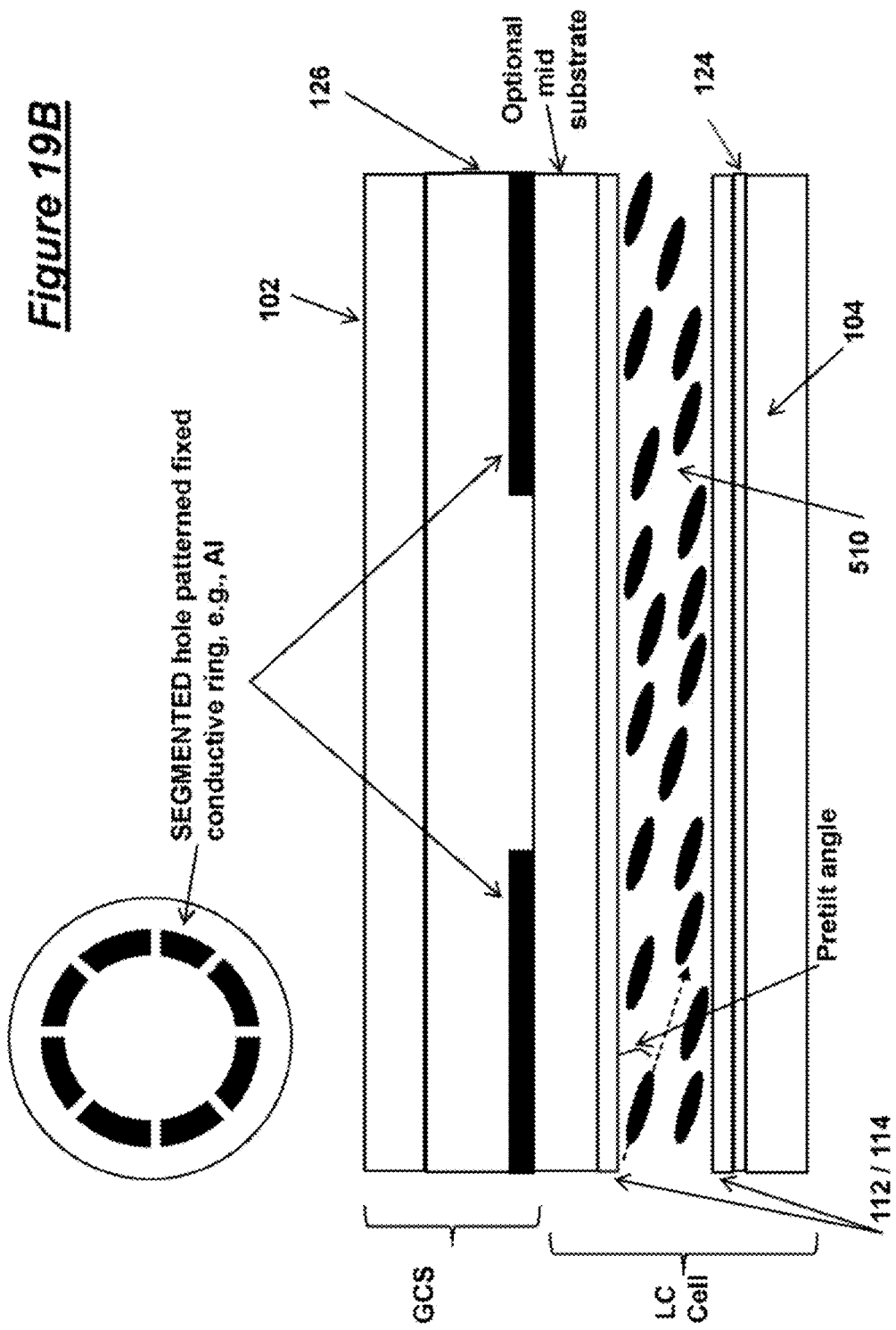
FIG. 19B is a schematic diagram illustrating another polarization dependent tunable liquid crystal lens layered structure of an intraocular device having a variable conductivity layer geometry in accordance with the proposed solution.

FIG. 19A illustrates a cross-section through a circular parametric TLCL intraocular device having a geometry similar to that illustrated in FIG. 5B wherein the highly resistive layer is replaced by a weakly conductive layer. FIG. 19B illustrates a cross-section through a circular parametric TLCL intraocular device having a geometry similar to that illustrated in FIG. 5B wherein the highly resistive layer is separated from the liquid crystal layer by a (buffer) mid substrate. Advantages of using a parametric TLCL include providing aberration correction corresponding to the optical power provided by the TLCL, for example via a lookup table.

Spit Cell Aberration Compensation

While some of the liquid crystal cells described above, and illustrated in the drawings, have a single orientation with two LC cells having orthogonal orientation for polarization independent operation, it will be appreciated that other arrangements are possible. For example, to provide for better angular independence of operation, multiple cells can provide opposed orientations for each polarization. An example of this is a split-cell design illustrated in FIG. 13A of commonly assigned International Patent Application PCT/CA2009/000743, the specification of which is incorporated herein by reference.

Figure 21:
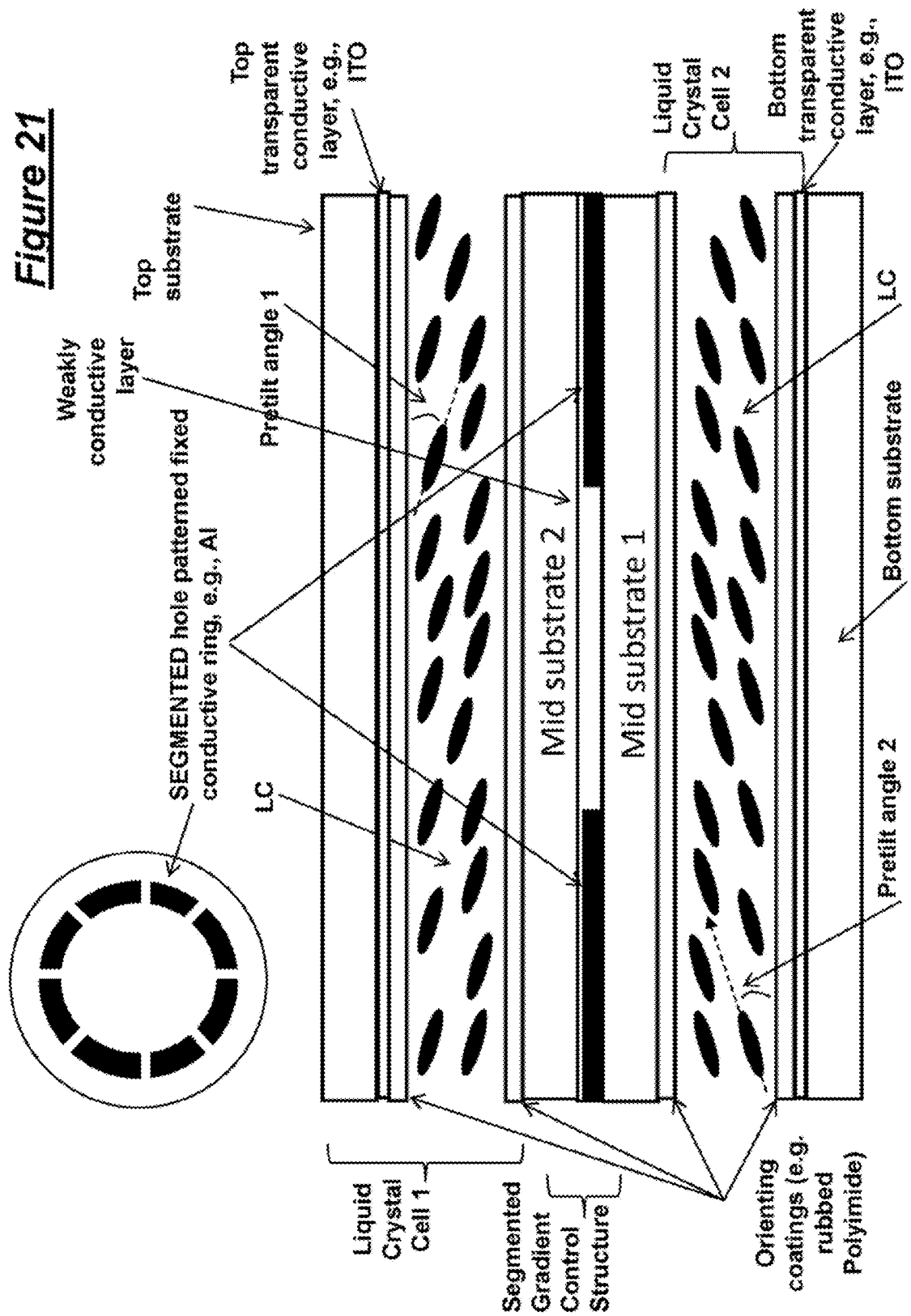
FIG. 21 is a schematic diagram illustrating another layered structure of a polarization dependent TLCL of an intraocular device having a split cell geometry in accordance with the proposed solution.

In accordance with an implementation of the proposed solution, FIG. 20 illustrates a layered structure of a polarization dependent TLCL of an intraocular device having a split cell geometry providing better angular independence. In accordance with another implementation, FIG. 21 illustrates a layered structure of a low voltage polarization dependent TLCL of an intraocular device having a split cell geometry. It will be understood that a polarization independent TLCL would include a pair of such layered structures with directors/alignment layers oriented at 90 degrees to each other.

Capacitively Coupled Electric Field Control

Figure 22A:
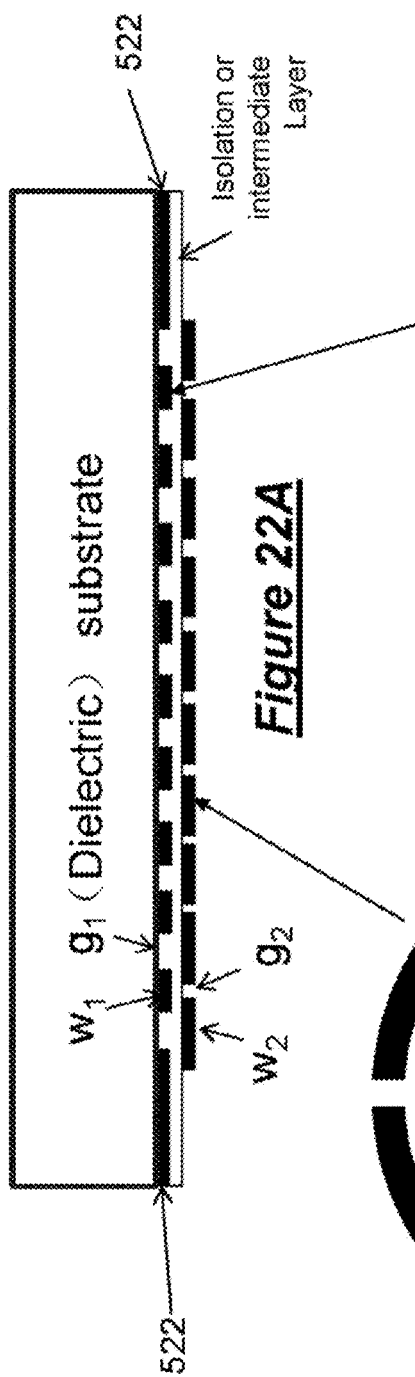
FIGS. 22A, 22B and 22C are schematic diagrams illustrating a segmented hole patterned electrode and corresponding electrically floating segmented concentric rings employed in the aperture of the hole patterned electrode in accordance with the proposed solution.
Figure 22C:
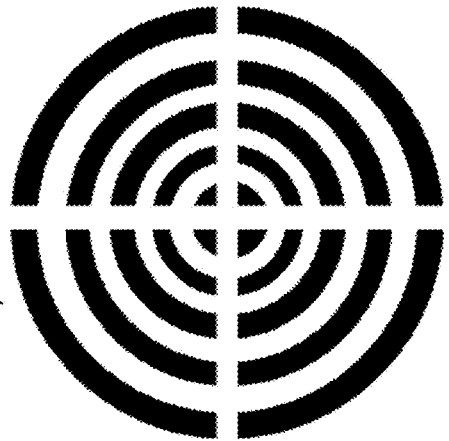
Figure 22B:
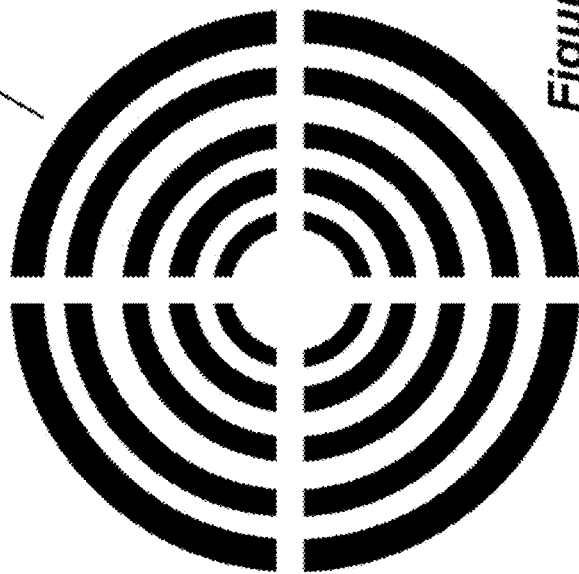

In accordance with another embodiment of the proposed solution, a parametric TLCL intraocular prosthesis is provided employing a hole patterned electrode having capacitively coupled transparent electrode ring pattern in the aperture. The electrically floating segmented electrodes capacitively couple by employing one of controlled superposition and weakly conductive material in electrical contact therewith to form a frequency dependent structure. With reference to FIGS. 22A, 22B and 22C at least one sector of concentric ring segments is electrically biased to compensate aberrations and to control the intraocular lens device.

Parametric Compensation of Birefringence Induced Offsets

Applicant has discovered that LC tunable lenses having two layers of liquid crystal can result in images that have an undesirable double vision due to a birefringence-induced image offset caused by each LC layer when such Tunable Liquid Crystal Lenses (TLCLs) are employed in the convergence space of the overall optical system including the intraocular prosthesis. Being employed in convergence space means that the TLCL is included towards the end or as the last optical element with respect to the propagation of the incident light. FIGS. 9A and 9B schematically illustrate image projection onto a retina in an eye employing a TLCL as the single or a rear optical element to correct/augment vision. In a human eye front optical elements include: glasses, contact lenses, the cornea, intraocular lenses such as inserted during cataract surgery and others. When used in an intraocular prosthesis, most refraction occurs ahead of the TLCL at the air-cornea surface and therefore the birefringence-induced image offset is a problem. This birefringence induced offset only happens for the polarization aligned with the liquid crystal molecules in each LC cell, and is dependent on the thickness of the LC layer and the angle of director orientation.

Figure 23:
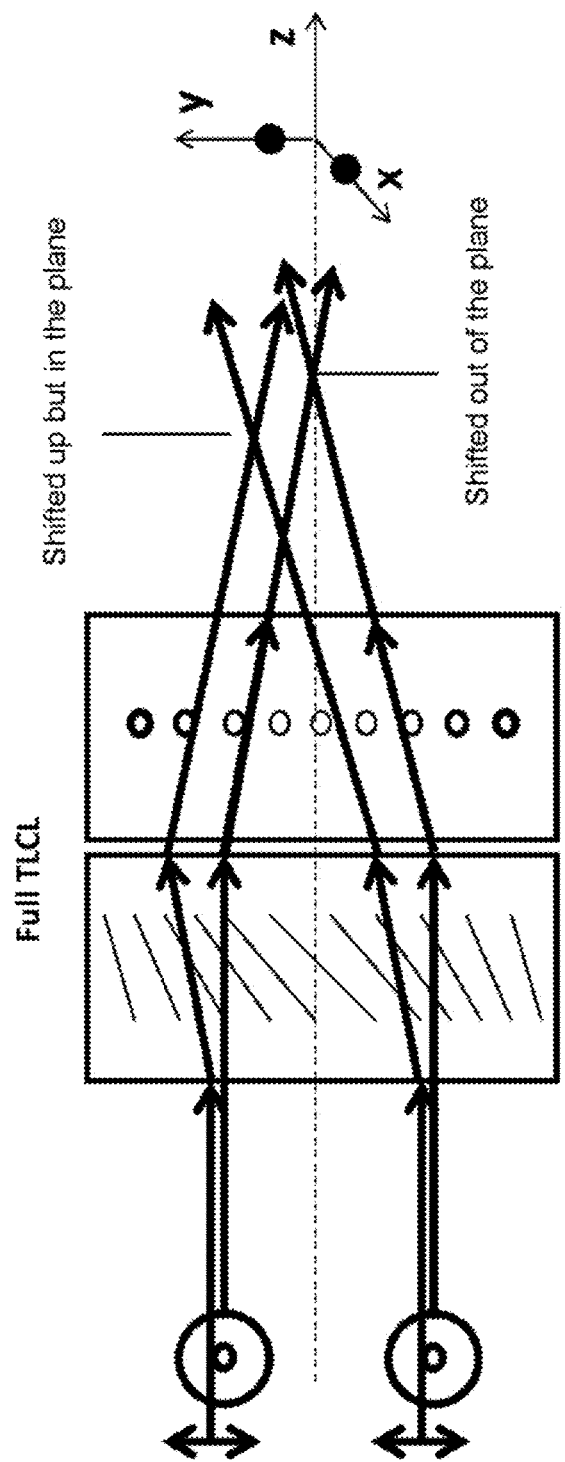
FIG. 23 is a schematic diagram illustrating birefringence-dependent focus offsets for both light polarization fields passing through a polarization independent TLCL.
Figure 24:
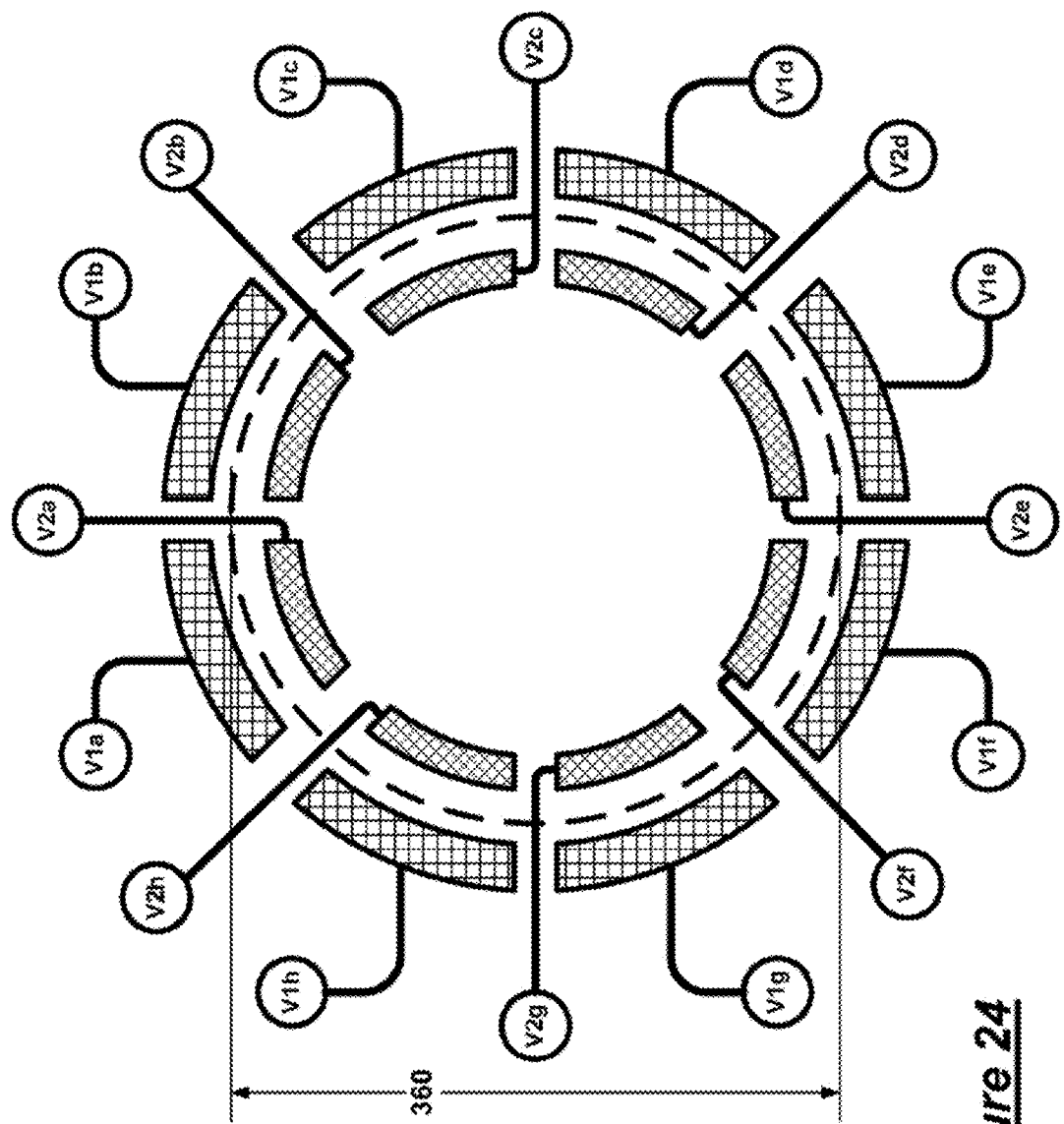
FIG. 24 is a schematic diagram illustrating a tunable liquid crystal lens intraocular device having both external and internal driven segmented electrodes in accordance with the proposed solution, wherein similar features bear similar labels throughout the drawings. Reference to "top" and "bottom" qualifiers in the present specification is made solely with reference to the orientation of the drawings as presented in the application and do not imply any absolute spatial orientation.

Light passing through a TLCL, as illustrated in FIG. 23 has the light of each polarization shifted differently, resulting in two small offsets. The effects of the birefringence induced offsets in a full TLCL illustrated in FIG. 23 are non-reversible, meaning that the actual sequence of half TLCL lenses matters. By positioning each LC layer (actually, it suffices to position the centers of the hole patterned electrodes) with respect to the other to have suitable offsets, the effect of birefringence induced offset can be reduced.

It will be appreciated that when opposed directions of LC director for each polarization are provided, as in FIG. 6, the birefringence induced offset of each LC layer is counterbalanced by the other LC layer of the same polarization, and the birefringence induced offset effect is also mitigated. This requires, of course, four LC layers.

The principles of operation described hereinabove can be implemented in a full TLCL intraocular prosthesis as follows:

Operational Characteristics

Tuneability of TLC lenses can be achieved through various drive signal modes, divided for ease of description herein, into: application of a variable voltage amplitude drive signal (fixed frequency amplitude modulation), and application of drive signals having a frequency and an amplitude. References are also made herein to applying a drive signal having a "variable frequency at fixed voltage" (fixed amplitude frequency modulation). A person of ordinary skill in the art would understand references to the "fixed voltage" in the context of a drive signal having a variable frequency, the drive signal having a fixed Root Means Square (RMS) voltage amplitude (Vrms). The frequency dependent material and/or structure can play an important role.

Voltage Amplitude Tuneability Control

In a TLCL driven via voltage amplitude modulation, LC molecules quickly align in response to an applied spatially modulated electric field created by the application of a voltage amplitude modulated drive signal across electrodes 124, 322. For example, in the case of a positive TLC lens, the highest optical power OPmax of such voltage controlled TLC lens is understood to be achieved as the applied voltage Vmax subjects the LC layer 510 to an electric field having the highest spatial variability for a given TLC geometry 400. This is provided by a strong electric field on the periphery and a weak electric field in the center. This spatial variability of the electric field in turn generates a corresponding non-uniform orientation of LC molecules greater at the periphery and lesser in the center.

Empirically, optical power decreases with increasing applied voltage amplitudes higher than Vmax. Higher voltages employed reduce the spatial variability of the electric field applied to the LC layer 510 compared to that applied by Vmax. The application of higher voltages leads to realigning LC molecules along electric field lines having lower alignment variability understood as a consequence of saturating the LC molecular reorientation across the LC layer.

Frequency Control Tuneability

A variable optical device controlling the propagation of light passing therethrough makes use of a frequency dependent material or structure, and an electrical signal generator generating a drive signal at a plurality of frequencies and amplitudes to modify a spatial profile of the electric field. An electrical signal generator generates drive signal components at a plurality of different frequency and voltage combinations and supplies a combined drive signal to the electrodes of the TLCL 400 so as to generate an electric field across LC layer 510.

The control signal for tuning the TLCL 400 is provided by a frequency control signal circuit configured to cause the TLC lens 400 to change the optical power and as a result tune the focus of an incident image of a scene.

TLC Frequency Response

At zero frequency and zero Vrms amplitude, the LC layer 510 is governed by the alignment layers 112 and 114. LC molecules are substantially aligned, for example at 3°. The index of refraction of the LC layer 510 has no variability. No lensing is provided by the LC layer 510, and therefore the TLCL 400 provides zero optical power. This ground state is a passive state governed by the physical properties of the geometry.

For a given (low) Vrms amplitude beyond an empirically determined threshold, an initial application of a relatively low frequency drive signal creates an effective uniform electrode profile across (into) the aperture 350 lifting LC molecules across the LC layer 510 out of the ground state to have an initial predominant orientation. The LC molecules will all be reoriented to have a common angular predominant orientation, for example 10° to 15° instead of the pre-tilt angle of about 3°. This state is an excited state governed by the properties of the variable conductivity layer including electrode 322 geometry and frequency dependent layer 426 charge mobility as described hereinabove.

For example, the optical power of such a TLC Lens can vary roughly from 8 to 16 diopters. However, operational limitations of a TLCL intraocular prosthesis such as limited size, limited power, operating temperature, biocompatibility, etc. reduce the optical power of a TLCL 500/600 having an accommodative clear aperture 360 of 4.5 mm to about at least 1.7 diopters. By employing a dual full TLCL 500/600 structure having an accommodative clear aperture 360 of 4.5 mm, the optical power of such intraocular prosthesis can be at least 3.5 diopters. Reducing the accommodative clear aperture 360 to about 3 mm, the optical power of a single full TLCL 500/600 can be at least 3.5 diopters, and at least 7 diopters for a dual full TLCL 500 intraocular prosthesis. A dual full TLCL structure 700 is illustrated schematically in FIG. 6.

While implementations of the proposed solution have been described employing a single drive signal having a single variable frequency drive signal component, the invention is not limited thereto. A multitude of variable frequency drive signal components can be mixed together and applied simultaneously to create a desired profile for the electric field (via the frequency dependent material and/or structure). In one implementation the multitude of frequencies combine to produce a pulse width modulated signal for which the filing factor can be varied. The filling factor can be modified to change the amount of high frequency content in the signal. Further details are provided in co-pending commonly assigned PCT/IB2009/052658 filed Jun. 21, 2009 which is incorporated herein by reference.

When the driving signal applied has a low frequency, an effective electrode is created which is substantially flat across the entire structure. This "horizontal" extension of the hole-patterned electrode 322 changes the electric field profile to be uniform as a result of the two effectively uniform electrode structures 322-426 and 124. Such a uniform field has a uniform aligning effect on the liquid crystal molecules so that any lensing effect is erased.

It has been discovered that the use of relatively low frequency drive signals reduces disclinations (orientation defects). Use of flat electric field profiles provided by low frequency drive signals allow the "erasure" of a lens. Therefore lens erasure can be provided at low frequency and low RMS voltages without necessitating additional electrodes or a drastic change in the driving voltage to very low (e.g., 0 Volts) or very high voltages (e.g., 100 Volts), which tend to reduce TLCL performance or violate voltage limits of a host device, such as an intraocular TLCL prosthesis.

It is understood, that the experimental results and manufacturing developments presented hereinabove provide reduction to practice at high optical powers, however for intraocular TLCL prostheses lower maximum Vrms amplitudes below 10V are used and frequencies in the order of 10 kHz.

Bipolar TLCL

In the above, extensive reference has been made to variable optical power TLCLs having unipolar (only positive or negative) optical power variability. TLCLs 300/400/500 can be manufactured or operated to exhibit both negative and positive optical power variability. For certainty, the invention is not limited unipolar TLCLs.

FIG. 7 schematically illustrates bipolar operation of a LC layer 510.

Wavefront Adjustment

It has been realized that a drastic radial drop in electric field strength across the LC layer generated by a hole patterned electrode and weakly conductive layer electric field control structure combination can cause departures from a spherical wavefront of a Liquid Crystal (LC) lens optical device. Such a LC lens subjects incident light to an aspherical wavefront which tends to have a flattened central top and a Gaussian-like drop-off towards the periphery. Depending on material properties of the LC lens and geometry parameters such as: the ratio between the hole patterned ring electrode diameter, electrode spacing, etc. the Modulation Transfer Function (MTF) of the LC lens in some cases provides either a central in-focus region within the clear aperture or a peripheral in-focus region within the clear aperture, this may be unacceptable for (large) millimeter size clear aperture applications, such as but not limited to intraocular devices, since it degrades significantly the modulation transfer function of the intraocular prosthesis in which the LC lens is employed.

As illustrated in FIG. 29, each electrode segment can divided into a pair of driven electrode segments, a radially outer electrode and a radially inner electrode. The voltages applied allow for control over the slope of the liquid crystal orientation profile at the outer edge of the lens. Not shown, a "floating" disc of transparent electrode can be arranged in a middle of the aperture to help reduce a radial drop in the electric field near the optical axis, as is known from PCT/CA2011/050783.

Those skilled in the art will recognize that the various principles and embodiments described herein may also be mixed and matched to create a TLC lens optical devices with various auto-focus characteristics. Electrodes of different shapes and configurations; frequency dependent materials of different types, shapes and positions; dual frequency liquid crystal materials of different types; different drive signal generators; etc. can be used in combination to create a TLC lens optical device with a particular characteristic. The TLC lens devices may be frequency controlled, voltage controlled, or controlled by a combination of the two.

While the invention has been shown and described with referenced to preferred embodiments thereof, it will be recognized by those skilled in the art that various changes in form and detail may be made therein without departing from the spirit and scope of the invention as defined by the appended claims.

What is claimed is:

1. A reprogrammable intraocular implant apparatus for replacing a natural lens of an eye, the apparatus having an encapsulated tunable liquid crystal optical device comprising:
   a variable optical power tunable liquid crystal lens having at least one segmented hole-patterned electrode, segments of the segmented hole-patterned electrode comprising a plurality of circumferentially adjacent circle sectors, wherein each of said plurality of circumferentially adjacent circle sectors are circumferentially separated by a gap, said tunable liquid crystal lens having an accommodation clear aperture;
   a tunable liquid crystal lens drive signal generator configured to generate a plurality of drive signals components, each drive signal component being configured to drive a corresponding hole-patterned electrode circle sector;

a tunable liquid crystal lens driver configured to control said drive signal generator to change a tunable liquid crystal lens optical power in response to at least one of a stimulus signal or an optical transfer function;

a remotely programmable tunable liquid crystal lens controller configured to recalibrate the tunable liquid crystal lens by adjusting the optical transfer function, adjusting at least one of the hole-patterned electrode circle sector's bias parameters, and adjusting a drive signal phase to compensate for dynamic adaptation of the eye over time;

a power store configured to store electrical power to drive said tunable liquid crystal lens, said generator, said driver and said controller; and a sensor component configured to provide said stimulus signal.

2. The apparatus of claim 1, said variable optical power tunable liquid crystal lens comprising at least one split liquid crystal cell, said split cell having a pair of liquid crystal layers, each liquid crystal layer being sandwiched between a pair of alignment layers, said pairs of alignment layers having opposite orientations.

3. The apparatus of claim 1, said encapsulated optical device being configured to fold for insertion into a region of said eye via an incision having at least one dimension smaller than a corresponding unfolded dimension of said optical device.

4. The apparatus of claim 1, said encapsulated optical device being one of sized to fit into a capsular bag of said natural lens and having outer dimensions smaller than dimensions of said natural lens.

5. The apparatus of claim 1, said optical device comprising a lens substrate deposited onto said tunable liquid crystal lens configured to at least one of augment said optical power of said tunable liquid crystal lens and shift a variability range of said optical power of said tunable liquid crystal lens.

6. The apparatus of claim 1, said tunable liquid crystal lens comprising a unipolar tunable liquid crystal lens configured to focus an image at infinity onto a retina of said eye under unpowered drive conditions and further configured to focus a near image onto said retina under high power drive conditions.

7. The apparatus of claim 1, said tunable liquid crystal lens comprising a bipolar tunable liquid crystal lens.

8. The apparatus of claim 7, said bipolar tunable liquid crystal lens being configured to focus one of a near image and an image at infinity onto a retina of said eye under a corresponding one of a negative optical power and a positive optical power under high power drive conditions.

9. The apparatus of claim 7, said bipolar tunable liquid crystal lens being configured to focus an image substantially at one of an arm's length, reading distance and working distance onto said retina under unpowered drive conditions at zero optical power.

10. The apparatus of claim 1, in providing said stimulus signal a said sensor component comprises an eye strain sensor configured to measure eye strain, and said tunable liquid crystal lens driver being configured to convert eye strain measurements into an optical power setting, said eye strain sensor further comprising a muscle tension sensor configured to measure eye strain by measuring muscle tension in a muscle, and said muscle comprising at least one of a ciliary muscle, an external eye muscle of said eye, and a muscle of an eyelid of said eye.

11. The apparatus of claim 1, said sensor component comprising an eyelid activity sensor configured to detect, from within said optical device, a degree of closure of an eyelid of said eye in providing said stimulus signal, and said tunable liquid crystal lens driver being configured to convert said degree of lid closure into an optical power setting, said eyelid activity sensor being configured to detect an eyelid shut condition of said eyelid, and said tunable liquid crystal lens controller being configured to shut down said tunable liquid crystal lens in response to said eyelid shut condition.

12. The apparatus of claim 1 comprising:

an electrical power coupler device configured to capture and store transmitted electrical power into said power storage, said electrical power coupler device comprising a receiver element encapsulated into said optical device, said receiver element being configured to receive radiated power and further configured to convert said radiated power into at least one of: electrical power for storage into said power storage and a programming signal, or said power coupler device comprising a resonant inductor encapsulated into said optical device, said inductor being configured to receive electrical power by induction and configured to convert said induced electrical power into electrical power for storage into said power storage, and said inductor comprising an induction coil driven externally; and an external power source configured to transmit electrical power, said external power source comprising an external transmitter element in at least one of an eye glass frame or an eye patch.

13. The apparatus of claim 1, said power storage comprises a rechargeable battery.

14. The apparatus of claim 1, wherein said remotely programmable tunable liquid crystal lens controller comprises a programming antenna providing a physical programming interface to said tunable liquid crystal lens controller.

15. The apparatus of claim 1, wherein said encapsulated tunable liquid crystal optical device comprises:

a substantially transparent encapsulating material configured to provide a fixed optical power element for augmenting said optical power of said tunable liquid crystal lens, said encapsulating material forming a lenticular shape at least over said accommodation clear aperture of the tunable liquid crystal lens, said encapsulating material encapsulating said drive signal generator, said driver, said controller, said power storage and said sensor component arranged about a periphery of said tunable liquid crystal lens, said optical power of said tunable liquid crystal lens being variable within a range, and said fixed optical power element being configured to scale said range.

16. The apparatus of claim 1 comprised by a reprogrammable intraocular implant system, the system further comprising:

a vision quality measurement apparatus configured to measure vision quality parameters of a patient having said reprogrammable intraocular implant apparatus;

a bias parameter or optical transfer function calculator configured to calculate data representing bias parameters or an optical transfer function from said vision quality parameters; and an intra-ocular lens (IOL) programming module configured to wirelessly transfer said data representing bias parameters or said optical transfer function to said remotely programmable tunable liquid crystal lens controller.

17. The apparatus of claim 16, wherein said bias parameter or optical transfer function calculator is configured to calculate the data representing bias parameters for each of said electrode circle sectors.

18. The apparatus of claim 16, wherein said bias parameter or optical transfer function calculator is configured to calculate the data representing said optical transfer function, and said remotely programmable tunable liquid crystal lens controller is configured to determine offset or bias parameters for each of said electrode circle sectors from said optical transfer function.

19. The apparatus of claim 16, wherein the IOL programming module is further configured to further transmit a variable optical power control signal, and the remotely programmable tunable liquid crystal lens controller is configured to adjust an optical power of the tunable liquid crystal lens according to the variable optical power control signal.

20. The apparatus of claim 1 wherein the sensor component includes at least one coil sensitive to varying magnetic fields indicative of varying angular degrees.

21. The apparatus of claim 1 wherein said circle sectors are disposed a same radial distance from a common center hole.

22. The apparatus of claim 1 wherein each of said circle sectors comprise a plurality of radially spaced electrode segments, wherein each of said radially spaced electrode segments are radially separated by a gap.

23. A reprogrammable intraocular implant apparatus for replacing a natural lens of an eye, the apparatus having an encapsulated tunable liquid crystal optical device comprising:
- a variable optical power tunable liquid crystal lens having at least one segmented hole-patterned electrode, said tunable liquid crystal lens having an accommodation clear aperture;
- a tunable liquid crystal lens drive signal generator configured to generate a plurality of drive signal components, each drive signal component being configured to drive a corresponding hole-patterned electrode segment;
- a tunable liquid crystal lens driver configured to control said drive signal generator to change a tunable liquid crystal lens optical power in response to one of a stimulus signal and an optical transfer function;
- a remotely programmable tunable liquid crystal lens controller configured to recalibrate the tunable liquid crystal lens by adjusting the optical transfer function, adjusting at least one of the hole-patterned electrode segment's bias parameters, and adjusting a drive signal phase to compensate for dynamic adaptation of the eye over time;
- a power store configured to store electrical power to drive said tunable liquid crystal lens, said generator, said driver and said controller; and
- a physiological change sensor component configured to provide said stimulus signal, said sensor component comprising an eyelid activity sensor configured to detect, from within said optical device, a degree of closure of an eyelid of said eye in providing said stimulus signal, and said tunable liquid crystal lens driver being configured to convert said degree of lid closure into an optical power setting, said eyelid activity sensor being configured to detect an eyelid shut condition of said eyelid, and said tunable liquid crystal lens controller being configured to shut down said tunable liquid crystal lens in response to said eyelid shut condition, said eyelid activity sensor comprising: at least one photosensor measuring light falling thereon; and at least one sensor coil encapsulated into said optical device and at least one magnetic bead affixed to said eyelid, said magnetic bead comprising a magnetic bead implant.

* * * * *